US009597288B2

(12) United States Patent
Finn et al.

(10) Patent No.: US 9,597,288 B2
(45) Date of Patent: Mar. 21, 2017

(54) TRANSMUCOSAL DELIVERY DEVICES WITH ENHANCED UPTAKE

(71) Applicant: BioDelivery Sciences International, Inc., Raleigh, NC (US)

(72) Inventors: Andrew Finn, Raleigh, NC (US); Niraj Vasisht, Cary, NC (US)

(73) Assignee: BioDelivery Sciences International, Inc., Raleigh, NC (US)

( * ) Notice: Subject to any disclaimer, the term of this patent is extended or adjusted under 35 U.S.C. 154(b) by 0 days.

(21) Appl. No.: 15/198,961

(22) Filed: Jun. 30, 2016

(65) Prior Publication Data

US 2016/0310409 A1 Oct. 27, 2016

Related U.S. Application Data

(63) Continuation of application No. 14/746,168, filed on Jun. 22, 2015, which is a continuation of application No. 13/413,112, filed on Mar. 6, 2012, now abandoned, which is a continuation of application No. 13/184,306, filed on Jul. 15, 2011, now Pat. No. 8,147,866, which is a continuation of application No. 11/817,915, filed as application No. PCT/US2007/016634 on Jul. 23, 2007, now abandoned.

(60) Provisional application No. 60/839,504, filed on Aug. 23, 2006, provisional application No. 60/832,726, filed on Jul. 21, 2006, provisional application No. 60/832,725, filed on Jul. 21, 2006.

(51) Int. Cl.
| | |
|---|---|
| *A61P 25/04* | (2006.01) |
| *A61K 31/485* | (2006.01) |
| *A61K 9/70* | (2006.01) |
| *A61K 9/00* | (2006.01) |
| *A61K 31/4468* | (2006.01) |

(52) U.S. Cl.
CPC ............ *A61K 9/006* (2013.01); *A61K 9/7007* (2013.01); *A61K 31/4468* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 3,640,741 A | 2/1972 | Etes | |
| 3,996,934 A | 12/1976 | Zaffaroni | |
| 4,226,848 A | 10/1980 | Nagai et al. | |
| 4,250,163 A | 2/1981 | Nagai et al. | |
| 4,285,934 A | 8/1981 | Tinnell | |
| 4,286,592 A | 9/1981 | Chandrasekaran | |
| 4,292,299 A | 9/1981 | Suzuki et al. | |
| 4,381,296 A | 4/1983 | Tinnell | |
| 4,517,173 A | 5/1985 | Kizawa et al. | |
| 4,518,721 A | 5/1985 | Dhabhar et al. | |
| 4,552,751 A | 11/1985 | Inaba et al. | |
| 4,572,832 A | 2/1986 | Kigasawa et al. | |
| 4,582,835 A | 4/1986 | Lewis et al. | |
| 4,594,240 A | 6/1986 | Kawata et al. | |
| 4,668,232 A | 5/1987 | Cordes et al. | |
| 4,713,239 A | 12/1987 | Babaian et al. | |
| 4,713,243 A | 12/1987 | Schiraldi et al. | |
| 4,713,246 A | 12/1987 | Begum et al. | |
| 4,715,369 A | 12/1987 | Suzuki et al. | |
| 4,720,387 A | 1/1988 | Sakamoto et al. | |
| 4,740,365 A | 4/1988 | Yukimatsu et al. | |
| 4,755,386 A | 7/1988 | Hsiao et al. | |
| 4,764,378 A | 8/1988 | Keith et al. | |
| 4,765,983 A | 8/1988 | Takayanagi et al. | |
| 4,784,858 A | 11/1988 | Ventouras | |
| 4,857,336 A | 8/1989 | Khanna et al. | |
| 4,867,970 A | 9/1989 | Newsham et al. | |
| 4,876,092 A | 10/1989 | Mizobuchi et al. | |
| 4,889,720 A | 12/1989 | Konishi | |
| 4,894,232 A | 1/1990 | Reul et al. | |
| 4,900,552 A | 2/1990 | Sanvordeker et al. | |
| 4,900,554 A | 2/1990 | Yanagibashi et al. | |
| 4,906,463 A | 3/1990 | Cleary et al. | |
| 4,915,948 A | 4/1990 | Gallopo et al. | |
| 4,990,339 A | 2/1991 | Scholl et al. | |
| 5,047,244 A | 9/1991 | Sanvordeker et al. | |

(Continued)

FOREIGN PATENT DOCUMENTS

| | | |
|---|---|---|
| AU | 741362 B2 | 11/2001 |
| CA | 2169729 A1 | 2/1995 |

(Continued)

OTHER PUBLICATIONS

Actiq Product Label, Approved Sep. 24, 2004 (Drug first approved Nov. 4, 1998); 31 pages.
BioDelivery Sciences International Press Release Dated Nov. 1, 2005, 2 pages.
BioDelivery Sciences International Press Release, Dated Apr. 24, 2006, 2 pages.
BioDelivery Sciences International Press Release, Dated Mar. 7, 2005, 2 pages.
BioDelivery Sciences International Press Release, Dated May 22, 2006, 2 pages.
BioDelivery Sciences International, The Wall Street Analyst Forum, Nov. 29, 2005.

(Continued)

*Primary Examiner* — Abigail Fisher
(74) *Attorney, Agent, or Firm* — McCarter & English LLP; Danielle L. Herritt; Wei Song

(57) ABSTRACT

The present invention provides methods for enhancing transmucosal uptake of a medicament, e.g., fentanyl or buprenorphine, to a subject and related devices. The method includes administering to a subject a transmucosal drug delivery device comprising the medicament. Also provided are devices suitable for transmucosal administration of a medicament to a subject and methods of their administration and use. The devices include a medicament disposed in a mucoadhesive polymeric diffusion environment and a barrier environment.

30 Claims, 4 Drawing Sheets

(56) References Cited

U.S. PATENT DOCUMENTS

| | | |
|---|---|---|
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,149,538 A | 9/1992 | Granger et al. |
| 5,166,233 A | 11/1992 | Kuroya et al. |
| 5,192,802 A | 3/1993 | Rencher |
| 5,196,202 A | 3/1993 | Konishi |
| 5,202,128 A | 4/1993 | Morella et al. |
| 5,236,714 A | 8/1993 | Lee et al. |
| 5,254,345 A | 10/1993 | Pogany et al. |
| 5,254,346 A | 10/1993 | Tucker et al. |
| 5,288,497 A | 2/1994 | Stanley et al. |
| 5,288,498 A | 2/1994 | Stanley et al. |
| 5,298,256 A | 3/1994 | Flockhart et al. |
| 5,298,258 A | 3/1994 | Akemi et al. |
| 5,314,915 A | 5/1994 | Rencher |
| 5,332,576 A | 7/1994 | Mantelle |
| 5,346,701 A | 9/1994 | Heiber et al. |
| 5,436,701 A | 7/1995 | Shimojo et al. |
| 5,462,749 A | 10/1995 | Rencher |
| 5,466,465 A | 11/1995 | Royds et al. |
| 5,505,956 A | 4/1996 | Kim et al. |
| 5,516,523 A | 5/1996 | Heiber et al. |
| 5,540,930 A | 7/1996 | Guy et al. |
| 5,599,554 A | 2/1997 | Majeti |
| 5,603,947 A | 2/1997 | Wong et al. |
| 5,679,714 A | 10/1997 | Weg |
| 5,700,478 A | 12/1997 | Biegajski et al. |
| 5,723,143 A | 3/1998 | Jacques et al. |
| 5,750,136 A | 5/1998 | Scholz et al. |
| 5,780,047 A | 7/1998 | Kamiya et al. |
| 5,785,989 A | 7/1998 | Stanley et al. |
| 5,800,832 A | 9/1998 | Tapolsky et al. |
| 5,849,322 A | 12/1998 | Ebert et al. |
| 5,853,760 A | 12/1998 | Cremer |
| 5,855,908 A | 1/1999 | Stanley et al. |
| 5,900,247 A | 5/1999 | Rault et al. |
| 5,948,430 A | 9/1999 | Zerbe et al. |
| 5,985,317 A | 11/1999 | Venkateshwaran et al. |
| 6,159,498 A | 12/2000 | Tapolsky et al. |
| 6,177,096 B1 | 1/2001 | Zerbe et al. |
| 6,200,604 B1 | 3/2001 | Pather et al. |
| 6,228,863 B1 | 5/2001 | Palermo et al. |
| 6,255,502 B1 | 7/2001 | Penkler et al. |
| 6,264,980 B1 | 7/2001 | Hille |
| 6,264,981 B1 | 7/2001 | Zhang et al. |
| 6,277,384 B1 | 8/2001 | Kaiko et al. |
| 6,284,262 B1 | 9/2001 | Place |
| 6,375,957 B1 | 4/2002 | Kaiko et al. |
| 6,475,494 B2 | 11/2002 | Kaiko et al. |
| 6,552,024 B1 | 4/2003 | Chen et al. |
| 6,562,363 B1 | 5/2003 | Mantelle et al. |
| 6,582,724 B2 | 6/2003 | Hsu et al. |
| 6,585,997 B2 | 7/2003 | Moro et al. |
| 6,592,887 B2 | 7/2003 | Zerbe et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,719,997 B2 | 4/2004 | Hsu et al. |
| 6,759,059 B1 | 7/2004 | Pettersson et al. |
| 6,780,504 B2 | 8/2004 | Rupprecht et al. |
| 6,835,392 B2 | 12/2004 | Hsu et al. |
| 6,969,374 B2 | 11/2005 | Krantz et al. |
| 7,144,587 B2 | 12/2006 | Oshlack et al. |
| 7,157,103 B2 | 1/2007 | Sackler |
| 7,172,767 B2 | 2/2007 | Kaiko et al. |
| 7,579,019 B2 | 8/2009 | Tapolsky et al. |
| 8,147,866 B2 | 4/2012 | Finn et al. |
| 2002/0034554 A1 | 3/2002 | Hsu et al. |
| 2002/0058068 A1 | 5/2002 | Houze et al. |
| 2002/0142036 A1 | 10/2002 | Rupprecht et al. |
| 2002/0160043 A1 | 10/2002 | Coleman |
| 2003/0044446 A1 | 3/2003 | Moro et al. |
| 2003/0104041 A1 | 6/2003 | Hsu et al. |
| 2003/0124176 A1 | 7/2003 | Hsu et al. |
| 2003/0161870 A1 | 8/2003 | Hsu et al. |
| 2003/0170195 A1 | 9/2003 | Houze et al. |
| 2003/0194420 A1 | 10/2003 | Holl et al. |
| 2004/0018241 A1 | 1/2004 | Houze et al. |
| 2004/0024003 A1 | 2/2004 | Asmussen et al. |
| 2004/0033255 A1 | 2/2004 | Baker et al. |
| 2004/0110781 A1 | 6/2004 | Harmon et al. |
| 2004/0126323 A1 | 7/2004 | Shevchuk et al. |
| 2004/0126416 A1 | 7/2004 | Reidenberg et al. |
| 2004/0151774 A1 | 8/2004 | Pauletti et al. |
| 2004/0180080 A1 | 9/2004 | Furusawa et al. |
| 2004/0191301 A1 | 9/2004 | Van Duren |
| 2004/0213828 A1 | 10/2004 | Smith |
| 2004/0219195 A1 | 11/2004 | Hart et al. |
| 2004/0219196 A1 | 11/2004 | Hart et al. |
| 2004/0220262 A1 | 11/2004 | Hsu et al. |
| 2004/0241218 A1 | 12/2004 | Tavares et al. |
| 2005/0002997 A1 | 1/2005 | Howard et al. |
| 2005/0013845 A1 | 1/2005 | Warren et al. |
| 2005/0037055 A1 | 2/2005 | Yang et al. |
| 2005/0042281 A1 | 2/2005 | Singh et al. |
| 2005/0048102 A1 | 3/2005 | Tapolsky et al. |
| 2005/0074487 A1 | 4/2005 | Hsu et al. |
| 2005/0085440 A1 | 4/2005 | Birch et al. |
| 2005/0169977 A1 | 8/2005 | Kanios et al. |
| 2005/0222135 A1 | 10/2005 | Buschmann et al. |
| 2006/0003008 A1 | 1/2006 | Gibson et al. |
| 2006/0051413 A1 | 3/2006 | Chow et al. |
| 2006/0069086 A1 | 3/2006 | Michalow |
| 2006/0073102 A1 | 4/2006 | Huaihung et al. |
| 2006/0073189 A1 | 4/2006 | Pinney et al. |
| 2006/0130828 A1 | 6/2006 | Sexton et al. |
| 2007/0148097 A1 | 6/2007 | Finn et al. |
| 2007/0149731 A1 | 6/2007 | Myers |
| 2007/0207192 A1 | 9/2007 | Holl et al. |
| 2008/0160068 A1 | 7/2008 | Hille et al. |
| 2008/0254105 A1 | 10/2008 | Tapolsky et al. |
| 2008/0317828 A1 | 12/2008 | Furusawa et al. |
| 2009/0270438 A1 | 10/2009 | Booles et al. |
| 2010/0003308 A1 | 1/2010 | Tapolsky et al. |
| 2010/0015183 A1 | 1/2010 | Finn et al. |
| 2010/0168147 A1 | 7/2010 | Chapleo et al. |
| 2011/0033541 A1 | 2/2011 | Myers et al. |
| 2011/0033542 A1 | 2/2011 | Myers et al. |
| 2011/0189259 A1 | 8/2011 | Vasisht et al. |
| 2011/0262522 A1 | 10/2011 | Finn et al. |
| 2012/0027839 A1 | 2/2012 | Tapolsky et al. |
| 2013/0045268 A1* | 2/2013 | Finn .................... A61K 31/485 424/443 |
| 2014/0178440 A1 | 6/2014 | Finn et al. |
| 2015/0246002 A1 | 9/2015 | Finn et al. |
| 2015/0366793 A1 | 12/2015 | Finn et al. |
| 2016/0095821 A1 | 4/2016 | Finn et al. |
| 2016/0101061 A1 | 4/2016 | Tapolsky et al. |
| 2016/0324768 A1 | 11/2016 | Finn et al. |

FOREIGN PATENT DOCUMENTS

| | | |
|---|---|---|
| CN | 101511337 A | 8/2009 |
| EP | 0 050 480 A2 | 4/1982 |
| EP | 069600 A2 | 1/1983 |
| EP | 0159604 A2 | 10/1985 |
| EP | 0 250 187 A2 | 12/1987 |
| EP | 0 262 422 A1 | 4/1988 |
| EP | 0 275 550 A1 | 7/1988 |
| EP | 0 381 194 A2 | 8/1990 |
| EP | 0 781 546 A1 | 7/1997 |
| EP | 1021204 A2 | 7/2000 |
| EP | 1105104 A1 | 6/2001 |
| EP | 1201233 A1 | 5/2002 |
| EP | 1642579 A1 | 4/2006 |
| GB | 981372 A | 1/1965 |
| GB | 2108841 A | 5/1983 |
| JP | 56-100714 A | 8/1981 |
| JP | 58-079916 A | 5/1983 |
| JP | 60-116630 A | 6/1985 |

(56) References Cited

FOREIGN PATENT DOCUMENTS

| | | |
|---|---|---|
| JP | 61-280423 A | 12/1986 |
| JP | 62-022713 A | 1/1987 |
| JP | 62-056420 A | 3/1987 |
| JP | 62-135417 A | 6/1987 |
| JP | 62-178513 A | 8/1987 |
| JP | 63-060924 A | 3/1988 |
| JP | 63-160649 A | 7/1988 |
| JP | 63-310818 A | 12/1988 |
| JP | 64-071812 | 3/1989 |
| JP | 1-226823 A | 9/1989 |
| JP | 3-246220 A | 11/1991 |
| JP | 4-059723 A | 2/1992 |
| JP | 9-504810 | 5/1997 |
| JP | 64-090121 | 4/1999 |
| JP | 2001-506640 | 5/2001 |
| JP | 2001-508037 A | 6/2001 |
| JP | 2002-526403 A | 8/2002 |
| JP | 2005-504763 A | 2/2005 |
| WO | 94/18925 A1 | 9/1994 |
| WO | 95/05416 A2 | 2/1995 |
| WO | 95/25544 A1 | 9/1995 |
| WO | 98/26780 A2 | 6/1998 |
| WO | 99/15210 A2 | 4/1999 |
| WO | 00/19987 | 4/2000 |
| WO | 00/42992 A2 | 7/2000 |
| WO | 01/30288 | 5/2001 |
| WO | 01/43728 | 6/2001 |
| WO | 01/58447 A1 | 8/2001 |
| WO | 01/85257 A2 | 11/2001 |
| WO | 02/092060 A1 | 11/2002 |
| WO | 03/013525 A1 | 2/2003 |
| WO | 03/013538 A1 | 2/2003 |
| WO | 03/070191 A2 | 8/2003 |
| WO | 2004/017941 A2 | 3/2004 |
| WO | 2005/016321 A1 | 2/2005 |
| WO | 2005/044243 A2 | 5/2005 |
| WO | 2005/055981 A2 | 6/2005 |
| WO | 2005/081825 A2 | 9/2005 |
| WO | 2007/007059 A1 | 1/2007 |
| WO | 2007/070632 A2 | 6/2007 |
| WO | 2008/011194 A2 | 1/2008 |
| WO | 2008/025791 A1 | 3/2008 |
| WO | 2008/040534 A2 | 4/2008 |
| WO | 2008/047163 A1 | 4/2008 |
| WO | 2008/100434 A1 | 8/2008 |
| WO | 2011/017484 A2 | 2/2011 |

OTHER PUBLICATIONS

Durfee et al., "Fentanyl Effervescent Buccal Tablets," American Journal of Drug Delivery, 2006, 4(1): 1-5.
Fentora Product Label, Approved Sep. 25, 2006 (Drug first approved Sep. 25, 2006); 41 pages.
Fine et al., "A Review of Oral Transmucosal Fentanyl Citrate: Potent, Rapid and Noninvasive Opioid Analgesia," Journal of Palliative Medicine, 1998, 1(1): 55-63.
Garrett et al., "Pharmacokinetics of morphine and its surrogates VI: Bioanalysis, solvokinetics, solubility, pKa values and protein binding of buprenorphine," Journal of Pharmaceutical Sciences, 1985, 74(5), pp. 515-524.
Guo J.-H. and Cooklock, K.M., "Bioadhesive polymer buccal patches for buprenorphine controlled delivery: solubility consideration" Drug Development and Industrial Pharmacy 21:2013-2019 (1995).
International Search Report and Written Opinion for International Application No. PCT/US2007/016634, dated Mar. 17, 2008. 14 pages.
McQuinn R.L. et al., "Sustained oral mucosal delivery in human volunteers of buprenorphine from a thin non-eroding mucoadhesive polymeric disk" Journal of Controlled Release 34:243-250 (1995).
Pather et al. "Enhanced Buccal Delivery of Fentanyl Using the OraVescent Drug Delivery System," Drug Delivery Tech. vol. 1, No. 1, Oct. 2001. Downloaded from www.drugdeliverytech.com, last accessed Dec. 20, 2010. 6 pages.
Robertson et al., "PK-PD modeling of buprenorphine in cats: intravenous and oral transmucosal administration," J. Vet. Pharmacol. Therap., 2005, 28, 453-460.
Roy et al., "Transdermal delivery of buprenorphine through cadaver skin," Journal of Pharmaceutical Sciences, 1994, 83(2), pp. 126-130.
Screenshots From www.fentora.com; pages downloaded Jul. 20, 2007, 6 pages.
Shi et al., "Studies on the Transoral Mucosal Absorption of Fentanyl", Chin. Pharm. J., 2005, vol. 40, No. 13, pp. 996-998.
Shojaei, A. et al., "Buccal Mucosa As a Route for System Drug Delivery: A Review," Journal of Pharmacy and Pharmaceutical Sciences (ualberta.ca/~csps), 1998, 1(1): 15-30.
Streisand et al. "Buccal Absorption of Fentanyl is pH dependent in Dogs," Anesthesiology, 82(3): 759-64 (1995).
Webster, L. (2006) Expert Opinion 15(11):1469-1473.
Weinberg, S. et al., "Sublingual absorption of selected opioid analgesics" Clin. Pharmacol. Ther. 44:335-342 (1988).
U.S. Appl. No. 15/213,051, filed Jul. 18, 2016, Pending.
U.S. Appl. No. 15/213,137, filed Jul. 18, 2016, Pending.
U.S. Appl. No. 14/875,107, filed Oct. 5, 2015, Pending.
"Defendant's initial invalidity contentions" United States District Court for the District of Delaware, C.A. No. 16-175-GMS, dated Oct. 28, 2016, 54 pages.
1999 Refresher Course Lecture and Clinical Update Index, retrieved online at http://anesthesia.stanford.edu/RCLS.pdf (1999).
Chiang et al., "Pharmacokinetics of the combination tablet of buprenorphine and naloxone," Drug and Alcohol Dependence 70 (2003) S39-S47.
Das et al., "Development of Mucoadhesive Dosage Forms of Buprenorphine for Sublingual Drug Delivery," Drug Delivery, pp. 89-95, 2004.
Extended European Search Report for European Patent Application No. 12860757.9 dated Jan. 20, 2016.
International Preliminary Report on Patentability for related PCT Application No. PCT/US2009/048325 dated Jan. 5, 2011.
International Search Report and Written Opinion for PCT/US2012/071330 dated Feb. 22, 2013.
International Search Report for Application No. PCT/US2006/047686, dated Aug. 13, 2007.
International Search Report for related PCT Application No. PCT/US2009/048325 dated Aug. 5, 2009.
Katz, Nathaniel, P. et al., "Anesthetic and Life Support Drugs Advisory Committee, Meeting, Wednesday, Jan. 2002," retrieved online at http://www.fda.gov/ohrms/dockets/ac/02/transcripts/3820t1.pdf (2002).
Lahmeyer, H.W. et al., "Pentazocine-naloxone: an 'abuse proof' drug can be abused," J. Clin. Psychopharmacol., vol. 6(6):389-390 (1986).
Meschia, et al., "Effect of Hormone Replacement Therapy and Calcitonin on Bone Mass in Postmenopausal Women" Eur J Obstet Gynecol Reprod Biol. Oct. 23, 1992;47(1):53-7.
Partial European Search Report for European Patent Application No. 12860757.9 dated Sep. 15, 2015.
The Merck Manual, http://www.merck.com/mmhe/sec06/ch078a.html?qt=pain&alt=sh, obtained online on Apr. 9, 2009.
U.S. Department of Justice, "Intelligence Bulletin, Buprenorphine: Potential for Abuse," retrieved online at http://www.usdoj.gov/ndic/pubs10/10123/10123p.pdf; Sep. 2004.
Webster's New World Dictionary (1988), V. Neufeldt ed. and D.B. Guralink ed., Prentice Hall: New York 3rd. College Ed., p. 505.
Written Opinion for related PCT Application No. PCT/US2009/048325 dated Aug. 5, 2009.

* cited by examiner

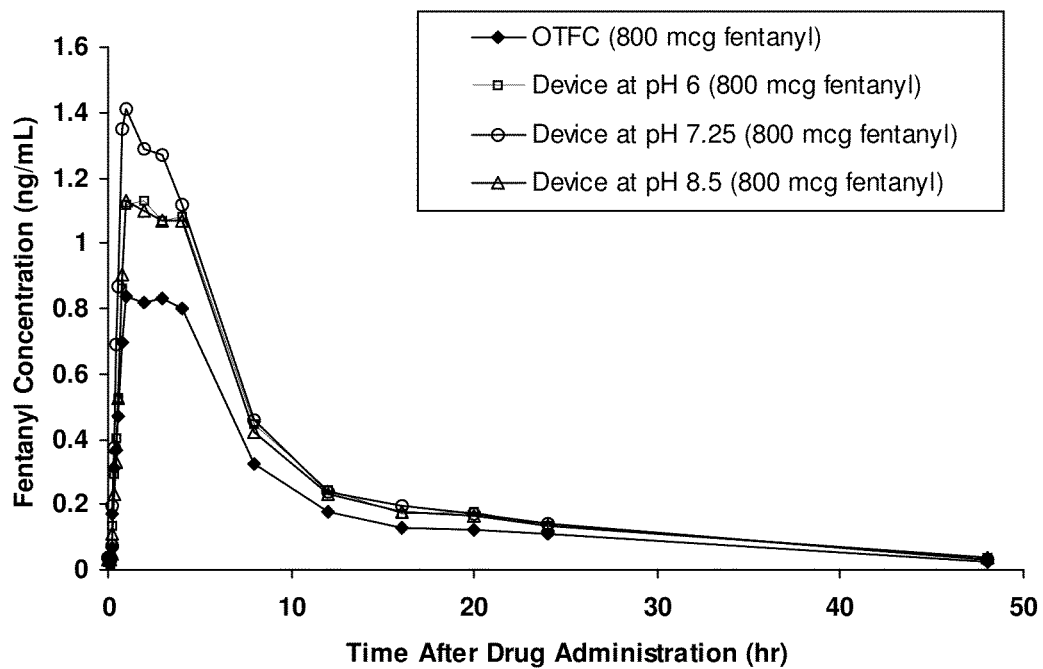
Figure 1. Mean Fentanyl Concentration-Time Plots For Three Exemplary Devices of the Invention and OTFC

Figure 2. Mean (SD) Fentanyl Concentration Over Time Comparing an Exemplary Device According To The Present Invention and OTFC
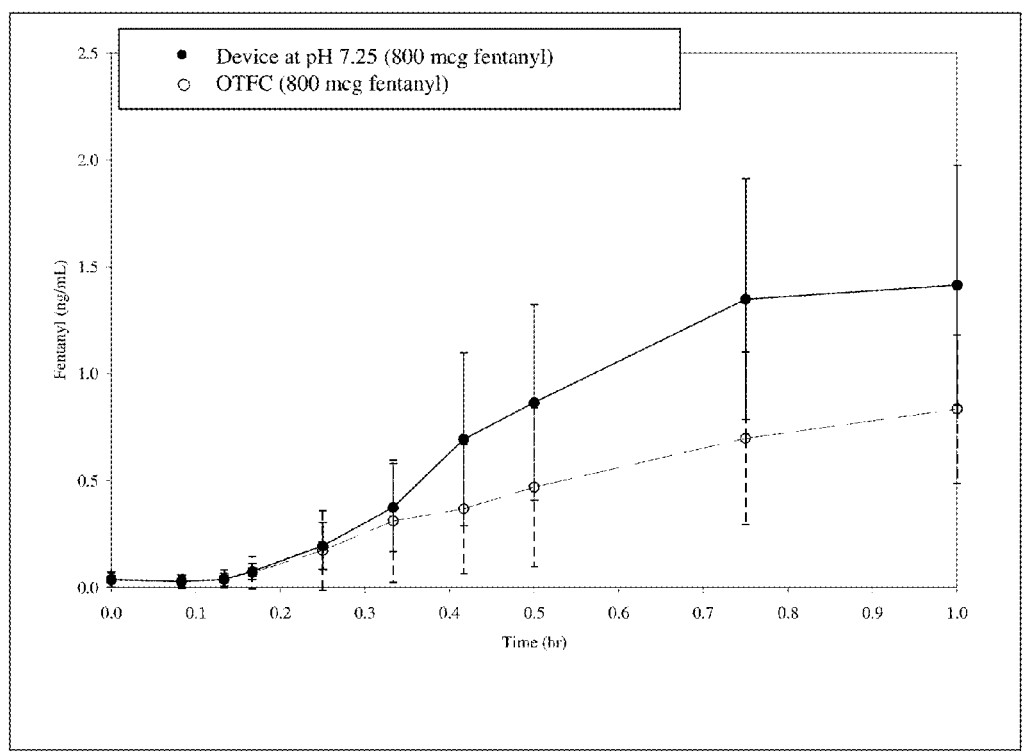

Figure 3. Mean (SD) Buprenorphine Concentration Over Time
Comparing an Exemplary Device According To The Present Invention and
Conventional Buprenorphine Delivery
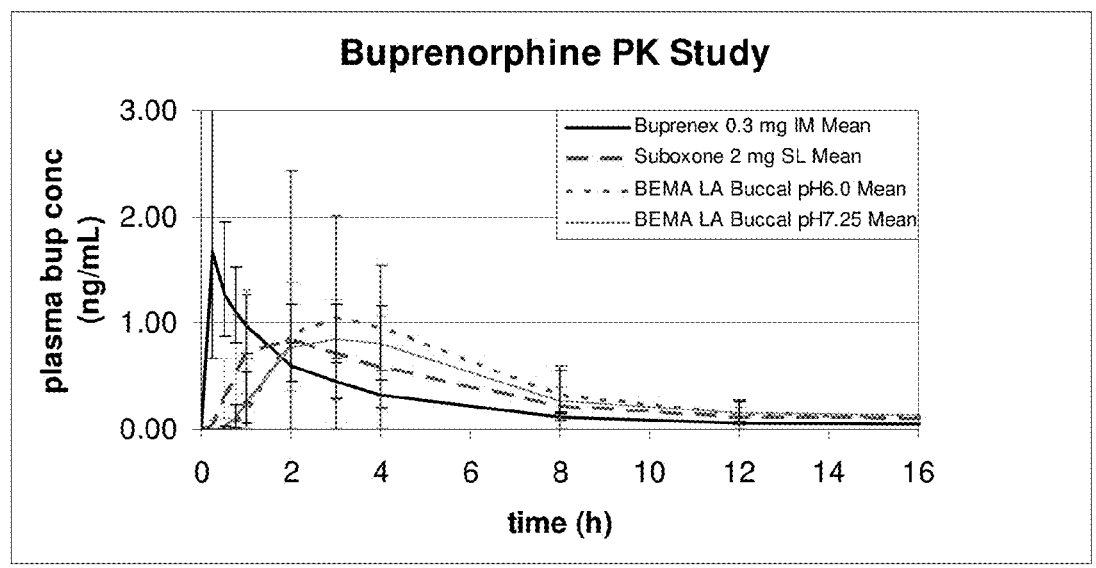

Figure 4: Exemplary Embodiments of the Present Invention

TRANSMUCOSAL DELIVERY DEVICES WITH ENHANCED UPTAKE

RELATED APPLICATIONS

This application is a continuation of U.S. patent application Ser. No. 14/746,168 filed Jun. 22, 2015, which is a continuation of U.S. patent application Ser. No. 13/413,112, filed Mar. 6, 2012, which is a continuation of U.S. patent application Ser. No. 13/184,306, filed Jun. 15, 2011, which is a continuation of U.S. patent application Ser. No. 11/817,915, filed Oct. 6, 2009, which is a U.S. National Phase of PCT/US2007/016634, filed Jul. 23, 2007. PCT/US2007/016634 claims priority to U.S. Provisional Application No. 60/832,725, filed Jul. 21, 2006, U.S. Provisional Application No. 60/832,726, filed Jul. 21, 2006, and U.S. Provisional Application No. 60/839,504, filed Aug. 23, 2006. The entire contents of these applications are incorporated herein by reference. This application is also related to U.S. Ser. No. 11/639,408, filed Dec. 13, 2006, and PCT/US2006/47686, also filed Dec. 13, 2006, both of which claim priority to U.S. Provisional Application No. 60/750,191, filed Dec. 13, 2005, and 60/764,618, filed Feb. 2, 2006. The entire contents of these applications are also incorporated herein by this reference.

BACKGROUND

U.S. Pat. No. 6,264,981 (Zhang et al.) describes delivery devices, e.g., tablets of compressed powders that include a solid solution micro-environment formed within the drug formulation. The micro-environment includes a solid pharmaceutical agent in solid solution with a dissolution agent that that facilitates rapid dissolution of the drug in the saliva. The micro-environment provides a physical barrier for preventing the pharmaceutical agent from being contacted by other chemicals in the formulation. The micro-environment may also create a pH segregation in the solid formulation. The pH of the micro-environment is chosen to retain the drug in an ionized form for stability purposes. The rest of the formulation can include buffers so that, upon dissolution in the oral cavity, the pH is controlled in the saliva such that absorption of the drug is controlled.

US Publication 2004/0253307 also describes solid dosage forms that include buffers that upon dissolution of the solid dosage form maintains the pharmaceutical agent at a desired pH to control absorption, i.e., to overcome the influence of conditions in the surrounding environment, such as the rate of saliva secretion, pH of the saliva and other factors.

BRIEF SUMMARY OF THE INVENTION

The present invention provides transmucosal devices for enhanced uptake of a medicament and methods of making and using the same. In some embodiments, the devices generally include a mucoadhesive polymeric diffusion environment that facilitates not only the absorption of the medicament across the mucosal membrane to which it is applied, but additionally, the permeability and/or motility of the medicament through the mucoadhesive polymeric diffusion environment to the mucosa.

Accordingly, in one embodiment, the present invention is directed to methods for enhancing direct transmucosal delivery of a fentanyl or fentanyl derivative to a subject. The method generally includes administering a bioerodable drug delivery device to an oral mucosal surface of the subject, the device comprising: a fentanyl or fentanyl derivative disposed in a mucoadhesive polymeric diffusion environment; and a barrier environment disposed relative to the polymeric diffusion environment such that a unidirectional gradient is created upon application to the mucosal surface and the fentanyl or fentanyl derivative is delivered to the subject.

In another embodiment, the present invention is directed to methods for treating pain in a subject. The method generally includes transmucosally administering to a subject a therapeutically effective amount of a fentanyl or fentanyl derivative disposed in a mucoadhesive polymeric diffusion environment such that the effective amount of the fentanyl or fentanyl derivative is delivered in less than about 30 minutes. In some embodiments, chronic pain is alleviated in the subject. In other embodiments, acute pain is alleviated in the subject. In other embodiments, the pain is breakthrough cancer pain.

In yet another embodiment, the present invention is directed to mucoadhesive delivery devices suitable for direct transmucosal administration of an effective amount of a fentanyl or fentanyl derivative to a subject. The mucoadhesive device generally includes a fentanyl or fentanyl derivative disposed in a polymeric diffusion environment; and a barrier environment disposed relative to the polymeric diffusion environment such that a unidirectional gradient is upon application to a mucosal surface.

In another embodiment, the present invention is directed to transmucosal delivery devices that deliver a fentanyl or fentanyl derivative with at least 50% direct buccal absorption and an absolute bioavailability of at least about 70%. In yet another embodiment, the present invention is directed to transmucosal delivery devices that deliver a fentanyl or fentanyl derivative directly to the mucosa to achieve onset of pain relief ($T_{first}$) of about 0.20 hours or less and time to peak plasma concentration ($T_{max}$) of about 1.6 hours or more. In still another embodiment, the present invention is directed to devices comprising about 800 µg of fentanyl, which exhibit upon transmucosal administration to a subject at least one in vivo plasma profile as follows: a $C_{max}$ of about 1.10 ng/mL or more; a $T_{first}$ of about 0.20 hours or less; and an $AUC_{0-24}$ of about 10.00 hr ng/mL or more. In yet another embodiment, the present invention is directed to transmucosal delivery devices which include a fentanyl or fentanyl derivative that delivers the fentanyl or fentanyl derivative in an amount effective to treat pain, wherein oral irritation, oral ulceration and/or constipation associated with the delivery of the fentanyl or fentanyl derivative is insignificant or eliminated. In one embodiment, the pH of the mucoadhesive polymeric diffusion environment is between about 6.5 and about 8, e.g., about 7.25. In one embodiment, the device comprises about 800 µg of fentanyl. In another embodiment, the device further comprises at least one additional layer that facilitates unidirectional delivery of the fentanyl or fentanyl derivative to the mucosa. In another embodiment, the fentanyl is fentanyl citrate.

In one embodiment, more than 30% of the fentanyl, e.g., more than 55% of the fentanyl, in the device becomes systemically available via mucosal absorption.

In one embodiment, the present invention is directed to methods for enhancing direct transmucosal delivery of buprenorphine to a subject. The method generally includes administering a bioerodable drug delivery device to an oral mucosal surface of the subject, the device comprising: buprenorphine disposed in a mucoadhesive polymeric diffusion environment; and a barrier environment disposed relative to the polymeric diffusion environment such that a unidirectional gradient is created upon application to the mucosal surface, and the buprenorphine is delivered to the subject.

In another embodiment, the present invention is directed to methods for treating pain in a subject. The method generally includes transmucosally administering to a subject a therapeutically effective amount of buprenorphine disposed in a mucoadhesive polymeric diffusion environment such that the effective amount of the buprenorphine is delivered in less than about 30 minutes. In some embodiments, chronic pain is alleviated in the subject. In other embodiments, acute pain is alleviated in the subject. In other embodiments, the pain is breakthrough cancer pain.

In yet another embodiment, the present invention is directed to mucoadhesive delivery devices suitable for direct transmucosal administration of an effective amount of buprenorphine to a subject. The mucoadhesive device generally includes buprenorphine disposed in a polymeric diffusion environment; and a barrier environment disposed relative to the polymeric diffusion environment such that a unidirectional gradient is created upon application to a mucosal surface. In one embodiment, the pH is between about 4.0 and about 7.5, e.g., about 6.0 or about 7.25. In another embodiment, the device further comprises at least one additional layer that facilitates unidirectional delivery of the buprenorphine to the mucosa.

In one embodiment of the methods and devices of the present invention, the device comprises a pH buffering agent. In one embodiment of the methods and devices of the present invention, the device is adapted for buccal administration or sublingual administration.

In one embodiment of the methods and devices of the present invention, the device is a mucoadhesive disc. In one embodiment of the methods and devices of the present invention, the medicament is formulated as a mucoadhesive film formed to delineate different dosages. In one embodiment of the methods and devices of the present invention, the device comprises a backing layer disposed adjacent to the mucoadhesive polymeric diffusion environment.

In one embodiment of the methods and devices of the present invention, the device further comprises an opioid antagonist. In one embodiment of the methods and devices of the present invention, the device further comprises naloxone.

In one embodiment of the methods and devices of the present invention, the device is a layered, flexible device. In one embodiment of the methods and devices of the present invention, the mucoadhesive polymeric diffusion environment has a buffered environment for the transmucosal administration.

In one embodiment of the methods and devices of the present invention, there is substantially no irritation at the site of transmucosal administration. In one embodiment of the methods and devices of the present invention, the subject experienced about a 50% decrease in pain over about 30 minutes.

In one embodiment of the methods and devices of the present invention, the polymeric diffusion environment comprises at least one ionic polymer system, e.g., polyacrylic acid (optionally crosslinked), sodium carboxymethylcellulose and mixtures thereof. In one embodiment, the polymeric diffusion environment comprises a buffer system, e.g., citric acid, sodium benzoate or mixtures thereof. In some embodiments, the device has a thickness such that it exhibits minimal mouth feel. In some embodiments, the device has a thickness of about 0.25 mm.

In some embodiments, the present invention provides a flexible, bioerodable mucoadhesive delivery device suitable for direct transmucosal administration of an effective amount of a fentanyl, fentanyl derivative, buprenorphine or buprenorphine derivative to a subject. The mucoadhesive device includes a mucoadhesive layer comprising a fentanyl, fentanyl derivative, buprenorphine or buprenorphine derivative disposed in a polymeric diffusion environment, wherein the polymeric diffusion environment has a pH of about 7.25 for the fentanyl or fentanyl derivative or a pH of about 6 for the buprenorphine or buprenorphine derivative; and a backing layer comprising a barrier environment which is disposed adjacent to and coterminous with the mucoadhesive layer. The device has no or minimal mouth feel and is able to transmucosally deliver the effective amount of the, fentanyl derivative, buprenorphine or buprenorphine derivative in less than about 30 minutes; and wherein a unidirectional gradient is created upon application of the device to a mucosal surface.

BRIEF DESCRIPTION OF THE DRAWINGS

The foregoing and other aspects, embodiments, objects, features and advantages of the invention can be more fully understood from the following description in conjunction with the accompanying figures.

FIGS. 1 and 2 are graphs comparing fentanyl citrate uptake in humans over 2 days post-administration, and 1 hour post-administration, respectively, for exemplary embodiments of the present invention and a commercially available delivery device (Actiq® Oral Transmucosal Fentanyl Citrate) as described in Examples 1 and 2.

FIG. 3 is a graph comparing buprenorphine uptake in humans over 16 hours post-administration, respectively, for exemplary embodiments of the present invention and a commercially available delivery devices as described in Examples 3 and 4.

DETAILED DESCRIPTION OF THE INVENTION

Figure 4A:
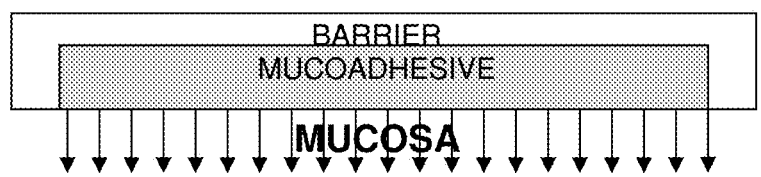
FIGS. 4A-C are schematic representations of exemplary embodiments of the present invention.

The present invention is based, at least in part, on the discovery that transmucosal uptake of medicaments can be enhanced by employing a novel polymeric diffusion environment. Such a polymeric diffusion environment is advantageous, e.g., because the absolute bioavailability of the medicament contained therein is enhanced, while also providing a rapid onset. Additionally, less medicament is needed in the device to deliver a therapeutic effect versus devices of the prior art. This renders the device less abusable, an important consideration when the medicament is a controlled substance, such as an opioid. The polymeric diffusion environment described in more detail herein, provides an enhanced delivery profile and more efficient delivery of the medicament. Additional advantages of a polymeric diffusion environment are also described herein.

In order to more clearly and concisely describe the subject matter of the claims, the following definitions are intended to provide guidance as to the meaning of terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

As used herein, the term "acute pain" refers to pain characterized by a short duration, e.g., three to six months. Acute pain is typically associated with tissue damage, and manifests in ways that can be easily described and observed. It can, for example, cause sweating or increased heart rate. Acute pain can also increase over time, and/or occur intermittently.

As used herein, the term "chronic pain" refers to pain which persists beyond the usual recovery period for an injury or illness. Chronic pain can be constant or intermittent. Common causes of chronic pain include, but are not limited to, arthritis, cancer, Reflex Sympathetic Dystrophy Syndrome (RSDS), repetitive stress injuries, shingles, headaches, fibromyalgia, and diabetic neuropathy.

As used herein, the term "breakthrough pain" refers to pain characterized by frequent and intense flares of moderate to severe pain which occur over chronic pain, even when a subject is regularly taking pain medication. Characteristics of breakthrough pain generally include: a short time to peak severity (e.g., three to five minutes); excruciating severity; relatively short duration of pain (e.g., 15 to 30 minutes); and frequent occurrence (e.g., one to five episodes a day). Breakthrough pain can occur unexpectedly with no obvious precipitating event, or it can be event precipitated. The occurrence of breakthrough pain is predictable about 50% to 60% of the time. Although commonly found in patients with cancer, breakthrough pain also occurs in patients with lower back pain, neck and shoulder pain, moderate to severe osteoarthritis, and patients with severe migraine.

As used herein, unless indicated otherwise, the term "fentanyl", includes any pharmaceutically acceptable form of fentanyl, including, but not limited to, salts, esters, and prodrugs thereof. The term "fentanyl" includes fentanyl citrate. As used herein, the term "fentanyl derivative" refers to compounds having similar structure and function to fentanyl. In some embodiments, fentanyl derivatives include those of the following formula:

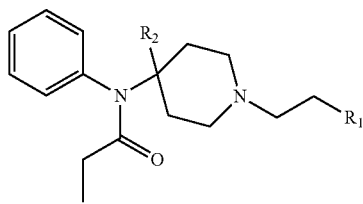

or pharmaceutically acceptable salts or esters thereof, wherein $R_1$ is selected from an aryl group, a heteroaryl group or a —COO—$C_{1-4}$ alkyl group; and $R_2$ is selected from —H, a —$C_{1-4}$ alkyl-O—$C_{1-4}$ alkyl group or a —COO—$C_{1-4}$ alkyl group.

Fentanyl derivatives include, but are not limited to, alfentanil, sufentanil, remifentanil and carfentanil.

As used herein, unless indicated otherwise, the term "buprenorphine", includes any pharmaceutically acceptable form of buprenorphine, including, but not limited to, salts, esters, and prodrugs thereof. As used herein, the term "buprenorphine derivative" refers to compounds having similar structure and function to buprenorphine. In some embodiments, fentanyl derivatives include those of the following formula:

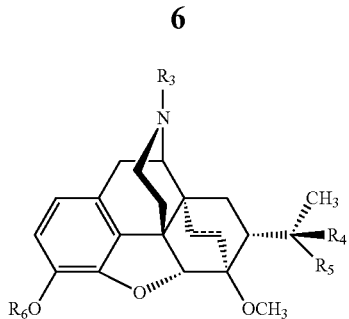

or pharmaceutically acceptable salts or esters thereof, wherein

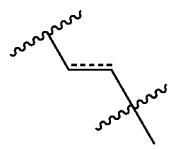

is a double or single bond; $R_3$ is selected from a —$C_{1-4}$ alkyl group or a cycloalkyl-substituted-$C_{1-4}$ alkyl group; $R_4$ is selected from a —$C_{1-4}$ alkyl; $R_5$ is —OH, or taken together, $R_4$ and $R_5$ form a =O group; and $R_6$ is selected from —H or a —$C_{1-4}$ alkyl group.

Buprenorphine derivatives include, but are not limited to, etorphine and diprenorphine.

As used herein, "polymeric diffusion environment" refers to an environment capable of allowing flux of a medicament to a mucosal surface upon creation of a gradient by adhesion of the polymeric diffusion environment to a mucosal surface. The flux of a transported medicament is proportionally related to the diffusivity of the environment which can be manipulated by, e.g., the pH, taking into account the ionic nature of the medicament and/or the ionic nature polymer or polymers included in the environment and.

As used herein, "barrier environment" refers to an environment in the form of, e.g., a layer or coating, capable of slowing or stopping flux of a medicament in its direction. In some embodiments, the barrier environment stops flux of a medicament, except in the direction of the mucosa. In some embodiments, the barrier significantly slows flux of a medicament, e.g., enough so that little or no medicament is washed away by saliva.

Figure 4B:
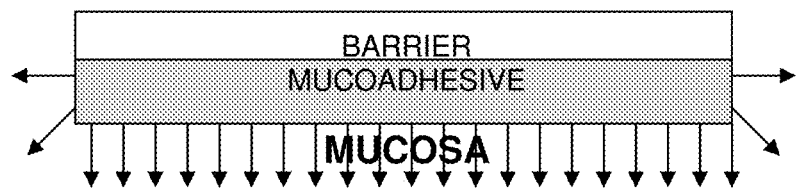
Figure 4C:
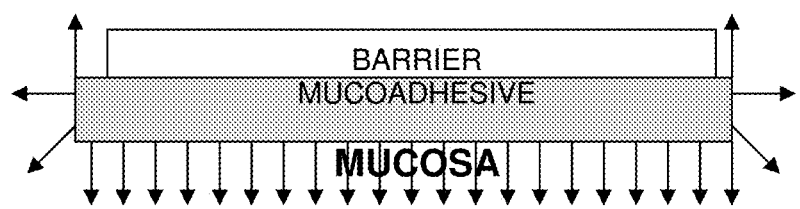

As used herein, the term "unidirectional gradient" refers to a gradient which allows for the flux of a medicament (e.g., fentanyl or buprenorphine) through the device, e.g., through a polymeric diffusion environment, in substantially one direction, e.g., to the mucosa of a subject. For example, the polymeric diffusion environment may be a mucoadhesive polymeric diffusion environment in the form of a layer or film disposed adjacent to a backing layer or film. Upon mucoadministration, a gradient is created between the mucoadhesive polymeric diffusion environment and the mucosa, and the medicament flows from the mucoadhesive polymeric diffusion environment, substantially in one direction towards the mucosa. In some embodiments, some flux of the medicament is not entirely unidirectional across the gradient; however, there is typically not free flux of the medicament in all directions. Such unidirectional flux is described in more detail herein, e.g., in relation to FIG. 4.

As used herein, "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder (e.g., to alleviate pain).

The term "subject" refers to living organisms such as humans, dogs, cats, and other mammals. Administration of the medicaments included in the devices of the present invention can be carried out at dosages and for periods of time effective for treatment of a subject. In some embodiments, the subject is a human. In some embodiments, the pharmacokinetic profiles of the devices of the present invention are similar for male and female subjects. An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

The term "transmucosal," as used herein, refers to any route of administration via a mucosal membrane. Examples include, but are not limited to, buccal, sublingual, nasal, vaginal, and rectal. In one embodiment, the administration is buccal. In one embodiment, the administration is sublingual. As used herein, the term "direct transmucosal" refers to mucosal administration via the oral mucosa, e.g., buccal and/or sublingual.

As used herein, the term "water erodible" or "at least partially water erodible" refers to a substance that exhibits a water erodibility ranging from negligible to completely water erodible. The substance may readily dissolve in water or may only partially dissolve in water with difficulty over a long period of time. Furthermore, the substance may exhibit a differing erodibility in body fluids compared with water because of the more complex nature of body fluids. For example, a substance that is negligibly erodible in water may show an erodibility in body fluids that is slight to moderate. However, in other instances, the erodibility in water and body fluid may be approximately the same.

The present invention provides transmucosal delivery devices that uniformly and predictably deliver a medicament to a subject. The present invention also provides methods of delivery of a medicament to a subject employing devices in accordance with the present invention. Accordingly, in one embodiment, the present invention is directed to mucoadhesive delivery devices suitable for direct transmucosal administration of an effective amount of a medicament, e.g., fentanyl or fentanyl derivative or buprenorphine to a subject. The mucoadhesive device generally includes a medicament disposed in a polymeric diffusion environment; and a having a barrier such that a unidirectional gradient is created upon application to a mucosal surface, wherein the device is capable of delivering in a unidirectional manner the medicament to the subject. The present invention also provides methods of delivery of a medicament to a subject employing the devices in accordance with the present invention.

In another embodiment, the present invention is directed to methods for enhancing direct transmucosal delivery of a medicament, e.g., fentanyl, fentanyl derivatives and/or buprenorphine, to a subject. The method generally includes administering a bioerodable drug delivery device to an oral mucosal surface of the subject, the device comprising: a medicament disposed in a mucoadhesive polymeric diffusion environment; and a barrier environment disposed relative to the polymeric diffusion environment such that a unidirectional gradient is created upon application to the mucosal surface, wherein an effective amount of the medicament is delivered to the subject.

In another embodiment, the present invention is directed to methods for treating pain in a subject. The method generally includes transmucosally administering to a subject a therapeutically effective amount of a medicament, e.g., fentanyl, fentanyl derivatives and/or buprenorphine, disposed in a mucoadhesive polymeric diffusion environment having a thickness such that the effective amount of the medicament is delivered in less than about 30 minutes and such that pain is treated. In some embodiments, the medicament is delivered in less than about 25 minutes. In some embodiments, the medicament is delivered in less than about 20 minutes.

In some embodiments of the above methods and devices, an effective amount is delivered transmucosally. In other embodiments, an effective amount is delivered transmucosally and by gastrointestinal absorption. In still other embodiments, an effective amount is delivered transmucosally, and delivery though the gastrointestinal absorption augments and/or maintains treatment, e.g., pain relief for a desired period of time, e.g., at least 1, 1.5, 2, 2.5, 3, 3.5, or 4 or more hours.

In yet another embodiment, the present invention is directed to transmucosal delivery devices that deliver a fentanyl or fentanyl derivative directly to the mucosa to achieve onset of pain relief ($T_{first}$) of about 0.20 hours or less and time to peak plasma concentration ($T_{max}$) of about 1.6 hours or more. The combination of a rapid onset with a delayed maximum concentration is particularly advantageous when treating pain, e.g., relief for breakthrough cancer pain (BTP) in opioid tolerant patients with cancer, because immediate relief is provided to alleviate a flare of moderate to severe pain but persistence is also provided to alleviate subsequent flares. Conventional delivery systems may address either the immediate relief or subsequent flare-ups, but the devices of this embodiment are advantageous because they address both.

TABLE 1

Selected Pharmacokinetic properties of transmucosal devices.

| | $T_{first}$ | $T_{max}$ | Total Bioavailability |
|---|---|---|---|
| BEMA pH 7.25 | 0.15 hours | 1.61 hours | 70% |
| Actiq ® | 0.23 hours | 2.28 hours | 47% |
| Fentora ® | 0.25 hours* | 0.50 hours | 65% |

*reported as onset of main relief, first time point measured.

The devices of the present invention may have a number of additional or alternative desirable properties, as described in more detail herein. Accordingly, in another embodiment, the present invention is directed to transmucosal delivery devices that deliver a fentanyl or fentanyl derivative with at least 50% direct buccal absorption and an absolute bioavailability of at least about 70%. In still another embodiment, the present invention is directed to devices comprising about 800 μg of fentanyl, which exhibit upon transmucosal administration to a subject at least one in vivo plasma profile as follows: a $C_{max}$ of about 1.10 ng/mL or more; a $T_{first}$ of about 0.20 hours or less; and an $AUC_{0-24}$ of about 10.00 hr·ng/mL or more.

The pain can be any pain known in the art, caused by any disease, disorder, condition and/or circumstance. In some embodiments, chronic pain is alleviated in the subject using the methods of the present invention. In other embodiments, acute pain is alleviated in the subject using the methods of the present invention. Chronic pain can arise from many sources including, cancer, Reflex Sympathetic Dystrophy Syndrome (RSDS), and migraine. Acute pain is typically directly related to tissue damage, and lasts for a relatively short amount of time, e.g., three to six months. In other embodiments, the pain is breakthrough cancer pain. In some embodiments, the methods and devices of the present invention can be used to alleviate breakthrough pain in a subject. For example, the devices of the present invention can be used to treat breakthrough pain in a subject already on chronic opioid therapy. In some embodiments, the devices and methods of the present invention provide rapid analgesia and/or avoid the first pass metabolism of fentanyl, thereby resulting in more rapid breakthrough pain relief than other treatments, e.g., oral medications.

In one embodiment of the methods and devices of the present invention, the subject experienced about a 50% decrease in pain over about 30 minutes. In one embodiment of the methods and devices of the present invention, the subject experienced about a 60% decrease in pain over about 30 minutes. In one embodiment of the methods and devices of the present invention, the subject experienced about a 70% decrease in pain over about 30 minutes. In one embodiment of the methods and devices of the present invention, the subject experienced about a 80% decrease in pain over about 30 minutes. In one embodiment of the methods and devices of the present invention, the subject experienced about a 90% decrease in pain over about 30 minutes. In one embodiment of the methods and devices of the present invention, the subject experienced about a 100% decrease in pain over about 30 minutes. In one embodiment of the methods and devices of the present invention, the subject experienced about a 50% decrease in pain over about 25 minutes. In one embodiment of the methods and devices of the present invention, the subject experienced about a 50% decrease in pain over about 20 minutes.

Without wishing to be bound by any particular theory, it is believed that delivery of the medicament is particularly effective because the mucoadhesive polymeric diffusion environment (e.g., the pH and the ionic nature of the polymers) is such that the medicament (e.g., a weakly basic drug such as fentanyl or buprenorphine) can rapidly move through the mucoadhesive polymeric diffusion environment to the mucosa, while also allowing efficient absorption by the mucosa. For example, in some embodiments, the pH is low enough to allow movement of the medicament, while high enough for absorption.

In some embodiments, the mucoadhesive polymeric diffusion environment is a layer with a buffered pH such that a desired pH is maintained at the mucosal administration site. Accordingly, the effect of any variation in pH encountered in a subject or between subjects (e.g., due to foods or beverages recently consumed), including any effect on uptake, is reduced or eliminated.

Accordingly, one advantage of the present invention is that variability in the properties of the device (e.g., due to changes in the pH of the ingredients) between devices, and from lot to lot is reduced or eliminated. Without wishing to be bound by any particular theory, it is believed that the polymeric diffusion environment of the present invention reduces variation, e.g., by maintaining a buffered pH. Yet another advantage is pH variability at the administration site (e.g., due to what food or drink or other medications was recently consumed) is reduced or eliminated, such that, e.g., the variability of the devices is reduced or eliminated.

A medicament for use in the present invention includes any medicament capable of being administered transmucosally. The medicament can be suitable for local delivery to a particular mucosal membrane or region, such as the buccal and nasal cavities, throat, vagina, alimentary canal or the peritoneum. Alternatively, the medicament can be suitable for systemic delivery via such mucosal membranes.

In one embodiment, the medicament can be an opioid. Opioids suitable for use in the present invention include, e.g., alfentanil, allylprodine, alphaprodine, apomorphine, anileridine, apocodeine, benzylmorphine, bezitramide, buprenorphine, butorphanol, clonitazene, codeine, cyclorphan, cyprenorphine, desomorphine, dextromoramide, dextropropoxyphene, dezocine, diampromide, diamorphone, dihydrocodeine, dihydromorphine, dimenoxadol, eptazocine, ethylmorphine, etonitazene, etorphine, fentanyl, fencamfamine, fenethylline, hydrocodone, hydromorphone, hydroxymethylmorphinan, hydroxypethidine, isomethadone, levomethadone, levophenacylmorphan, levorphanol, lofentanil, mazindol, meperidine, metazocine, methadone, methylmorphine, modafinil, morphine, nalbuphene, necomorphine, normethadone, normorphine, opium, oxycodone, oxymorphone, pholcodine, profadol remifentanil, sufentanil, tramadol, corresponding derivatives, physiologically acceptable compounds, salts and bases. In some embodiments, the medicament is fentanyl, e.g., fentanyl citrate. In some embodiments, the medicament is buprenorphine.

The amount of medicament, e.g. fentanyl or buprenorphine, to be incorporated into the device of the present invention depends on the desired treatment dosage to be administered, e.g., the fentanyl or fentanyl derivative can be present in about 0.001% to about 50% by weight of the device of the present invention, and in some embodiments between about 0.005 and about 35% by weight or the buprenorphine can be present in about 0.001% to about 50% by weight of the device of the present invention, and in some embodiments between about 0.005 and about 35% by weight. In one embodiment, the device comprises about 3.5% to about 4.5% fentanyl or fentanyl derivative by weight. In one embodiment, the device comprises about 3.5% to about 4.5% buprenorphine by weight. In another embodiment, the device comprises about 800 µg of a fentanyl such as fentanyl citrate. In another embodiment the device comprises about 25, 50, 75, 100, 150, 200, 300, 400, 500, 600, 700, 900, 1000, 1200, 1500, 1600 or 2000 µg of a fentanyl such as fentanyl citrate or fentanyl derivative. It is to be understood that all values and ranges between these values and ranges are meant to be encompassed by the present invention. In another embodiment, the device comprises about 800 µg of buprenorphine. In another embodiment the device comprises about 100, 200, 300, 400, 500, 600, 700, 900, 1000, 1200, 1500, or 2000 µg of buprenorphine. In another embodiment the device comprises about 25, 50, 75, 100, 150, 200, 300, 400, 500, 600, 700, 900, 1000, 1200, 1500, 1600 or 2000 µg of any of the medicaments described herein.

One approach to reaching an effective dose is through titration with multiple dosage units such that patients start with a single 200 mcg unit and progressively increase the number of units applied until reaching an effective dose or 800 mcg (4 units) dose as the multiple discs once an effective dose has been identified. Accordingly, in some embodiments, the methods of the present invention also include a titration phase to identify a dose that relieves pain and produces minimal toxicity, because the dose of opioid, e.g., fentanyl, required for control of breakthrough pain episodes is often not easily predicted. The linear relationship between surface area of the devices of the present invention and pharmacokinetic profile may be exploited in the dose titration process through the application of single or multiple discs to identify an appropriate dose, and then substitution of a single disc containing the same amount of medicament.

In one embodiment, the devices of the present invention are capable of delivering a greater amount of fentanyl systemically to the subject than conventional devices. According to the label for Actiq® Oral Transmucosal Fentanyl Citrate, approximately 25% of the fentanyl in the ACTIQ product is absorbed via the buccal mucosa, and of the remaining 75% that is swallowed, another 25% of the total fentanyl becomes available via absorption in the GI tract for a total of 50% total bioavailability. According to Fentora Fentanyl Buccal tablet literature, approximately 48% of the fentanyl in FENTORA product is absorbed via the buccal mucosa, and of the remaining 52%, another 17% of the total fentanyl becomes available via absorption in the GI tract for a total of 65% total bioavailability. Accordingly, in some embodiments, more than about 30% of the fentanyl disposed in the devices of the present invention becomes systemically available or bioavailable via absorption by the mucosa. In some embodiments, more than about 35%, 40%, 45%, 50%, 55%, 60%, 65%, 70%, 75% or 80% becomes systemically available via mucosal absorption. In some embodiments, more than about 55%, 60%, 65% or 70% of the fentanyl disposed in the devices of the present invention becomes systemically available or bioavailable by any route, mucosal and/or GI tract. In some embodiments, more than about 60%, 65%, 70%, 75%, 80%, 85%, 90%, or 95% becomes systemically available.

Accordingly, another advantage of the devices and methods of the present invention is that because the devices of the present invention more efficiently deliver the medicament, e.g., fentanyl or buprenorphine, than do conventional devices, less medicament can be included than must be included in conventional devices to deliver the same amount of medicament. Accordingly, in some embodiments, the devices of the present invention are not irritating to the mucosal surface on which it attaches. In some embodiments, the devices of the present invention cause little or no constipation, even when the devices include an opioid antagonist such as naloxone. In yet another embodiment, the present invention is directed to transmucosal delivery devices which include a fentanyl or fentanyl derivative that delivers the fentanyl or fentanyl derivative in an amount effective to treat pain, wherein oral irritation, oral ulceration and/or constipation associated with the delivery of the fentanyl or fentanyl derivative is not significant or eliminated.

Another advantage is the devices of the present invention are less subject to abuse than conventional devices because less medicament, e.g., fentanyl or buprenorphine, is required in the device, i.e., there is less medicament to be extracted by an abuser for injection into the bloodstream.

In some embodiments, the devices of the present invention have a dose response that is substantially directly proportional to the amount of medicament present in the device. For example, if the $C_{max}$ is 10 ng/mL for a 500 dose, then it is expected in some embodiments that a 1000 µg dose will provide a $C_{max}$ of approximately 20 ng/mL. Without wishing to be bound by any particular theory, it is believed that this is advantageous in determining a proper dose in a subject.

In some embodiments, the devices of the present invention further comprise an opioid antagonist in any of various forms, e.g., as salts, bases, derivatives, or other corresponding physiologically acceptable forms. Opioid antagonists for use with the present invention include, but are not limited to, naloxone, naltrexone, nalmefene, nalide, nalmexone, nalorphine, naluphine, cyclazocine, levallorphan and physiologically acceptable salts and solvates thereof, or combinations thereof. In one embodiment, the device further comprises naloxone.

In some embodiments, the properties of the polymeric diffusion environment are effected by its pH. In one embodiment, e.g., when the medicament is fentanyl, the pH of the mucoadhesive polymeric diffusion environment in the devices of the present invention is between about 6.5 and about 8. In another embodiment, the pH of the mucoadhesive polymeric diffusion environment is about 7.25. In another embodiment, the pH is between about 7.0 and about 7.5, or between about 7.25 and 7.5. In other embodiments, the pH is about 6.5, 7.0, 7.5, 8.0 or 8.5, or any incremental value thereof. It is to be understood that all values and ranges between these values and ranges are meant to be encompassed by the present invention.

In one embodiment, e.g., when the medicament is buprenorphine, the pH of the mucoadhesive polymeric diffusion environment in the devices of the present invention is between about 4.0 and about 7.5. In another embodiment, the pH of the mucoadhesive polymeric diffusion environment is about 6.0. In one embodiment, the pH of the mucoadhesive polymeric diffusion environment is about 5.5 to about 6.5, or between about 6.0 and 6.5. In yet another embodiment, the pH of the mucoadhesive polymeric diffusion environment is about 7.25. In another embodiment, the pH is between about 7.0 and 7.5, or between about 7.25 and 7.5. In other embodiments, the pH of the device may be about 4.0, 4.5, 5.0, 5.5, 6.0, 6.5, 7.0, or 7.5, or any incremental value thereof. It is to be understood that all values and ranges between these values and ranges are meant to be encompassed by the present invention.

The pH of the mucoadhesive polymeric diffusion environment can be adjusted and/or maintained by methods including, but not limited to, the use of buffering agents, or by adjusting the composition of the device of the present invention. For example, adjustment of the components of the device of the present invention that influence pH, e.g., the amount of anti-oxidant, such as citric acid, contained in the device will adjust the pH of the device.

In some embodiments, the properties of the polymeric diffusion environment are effected by its buffering capacity. In some embodiments, buffering agents are included in the mucoadhesive mucoadhesive polymeric diffusion environment. Buffering agents suitable for use with the present invention include, for example, phosphates, such as sodium phosphate; phosphates monobasic, such as sodium dihydrogen phosphate and potassium dihydrogen phosphate; phosphates dibasic, such as disodium hydrogen phosphate and dipotassium hydrogen phosphate; citrates, such as sodium citrate (anhydrous or dehydrate); bicarbonates, such as sodium bicarbonate and potassium bicarbonate may be used. In one embodiment, a single buffering agent, e.g., a dibasic buffering agent is used. In another embodiment, a combination of buffering agents is employed, e.g., a combination of a tri-basic buffering agent and a monobasic buffering agent.

In one embodiment, the mucoadhesive polymeric diffusion environment of the device will have a buffered environment, i.e., a stabilized pH, for the transmucosal administration of a medicament. The buffered environment of the device allows for the optimal administration of the medicament to a subject. For example, the buffered environment can provide a desired pH at the mucosa when in use, regardless of the circumstances of the mucosa prior to administration.

Accordingly, in various embodiments, the devices include a mucoadhesive polymeric diffusion environment having a buffered environment that reduces or eliminates pH variability at the site of administration due to, for example, medications, foods and/or beverages consumed by the subject prior to or during administration. Thus, pH variation encountered at the site of administration in a subject from one administration to the next may have minimal or no effect on the absorption of the medicament. Further, pH variation at the administration site between different patients will have little or no effect on the absorption of the medicament. Thus, the buffered environment allows for reduced inter- and intra-subject variability during transmucosal administration of the medicament. In another embodiment, the present invention is directed to methods for enhancing uptake of a medicament that include administering to a subject a device including a medicament disposed in a mucoadhesive polymeric diffusion environment having a buffered environment for the transmucosal administration. In yet another embodiment, the present invention is directed to methods of delivering a therapeutically effective amount of a medicament to a subject that include administering a device including a medicament disposed in a mucoadhesive polymeric diffusion environment having a buffered environment for the transmucosal administration.

The devices of the present invention can include any combination or sub-combination of ingredients, layers and/or compositions of, e.g., the devices described in U.S. Pat. No. 6,159,498, U.S. Pat. No. 5,800,832, U.S. Pat. No. 6,585,997, U.S. Pat. No. 6,200,604, U.S. Pat. No. 6,759,059 and/or PCT Publication No. WO 05/06321. The entire contents of these patent and publications are incorporated herein by reference in their entireties.

In some embodiments, the properties of the polymeric diffusion environment are effected by the ionic nature of the polymers employed in the environment. In one embodiment, the mucoadhesive polymeric diffusion environment is water-erodible and can be made from a bioadhesive polymer(s) and optionally, a first film-forming water-erodible polymer(s). In one embodiment, the polymeric diffusion environment comprises at least one ionic polymer system, e.g., polyacrylic acid (optionally crosslinked), sodium carboxymethylcellulose and mixtures thereof.

In some embodiments, the mucoadhesive polymeric diffusion environment can include at least one pharmacologically acceptable polymer capable of bioadhesion (the "bioadhesive polymer") and can optionally include at least one first film-forming water-erodible polymer (the "film-forming polymer"). Alternatively, the mucoadhesive polymeric diffusion environment can be formed of a single polymer that acts as both the bioadhesive polymer and the first film-forming polymer. Additionally or alternatively, the water-erodible mucoadhesive polymeric diffusion environment can include other first film-forming water-erodible polymer(s) and water-erodible plasticizer(s), such as glycerin and/or polyethylene glycol (PEG).

In some embodiments, the bioadhesive polymer of the water-erodible mucoadhesive polymeric diffusion environment can include any water erodible substituted cellulosic polymer or substituted olefinic polymer wherein the substituents may be ionic or hydrogen bonding, such as carboxylic acid groups, hydroxyl alkyl groups, amine groups and amide groups. For hydroxyl containing cellulosic polymers, a combination of alkyl and hydroxyalkyl groups will be preferred for provision of the bioadhesive character and the ratio of these two groups will have an effect upon water swellability and disperability. Examples include polyacrylic acid (PAA), which can optionally be partially crosslinked, sodium carboxymethyl cellulose (NaCMC), moderately to highly substituted hydroxypropylmethyl cellulose (HPMC), polyvinylpyrrolidone (PVP, which can optionally be partially crosslinked), moderately to highly substituted hydroxyethylmethyl cellulose (HEMC) or combinations thereof. In one embodiment, HEMC can be used as the bioadhesive polymer and the first film forming polymer as described above for a mucoadhesive polymeric diffusion environment formed of one polymer. These bioadhesive polymers are preferred because they have good and instantaneous mucoadhesive properties in a dry, system state.

The first film-forming water-erodible polymer(s) of the mucoadhesive polymeric diffusion environment can be hydroxyalkyl cellulose derivatives and hydroxyalkyl alkyl cellulose derivatives preferably having a ratio of hydroxyalkyl to alkyl groups that effectively promotes hydrogen bonding. Such first film-forming water-erodible polymer(s) can include hydroxyethyl cellulose (HEC), hydroxypropyl cellulose (HPC), hydroxypropylmethyl cellulose (HPMC), hydroxyethylmethyl cellulose (HEMC), or a combination thereof. Preferably, the degree of substitution of these cellulosic polymers will range from low to slightly above moderate.

Similar film-forming water-erodible polymer(s) can also be used. The film-forming water-erodible polymer(s) can optionally be crosslinked and/or plasticized in order to alter its dissolution kinetics.

In some embodiments, the mucoadhesive polymeric diffusion environment, e.g., a bioerodable mucoadhesive polymeric diffusion environment, is generally comprised of water-erodible polymers which include, but are not limited to, hydroxyethyl cellulose, hydroxypropyl cellulose, hydroxypropylmethyl cellulose, hydroxyethylmethyl cellulose, polyacrylic acid (PAA) which may or may not be partially crosslinked, sodium carboxymethyl cellulose (NaCMC), and polyvinylpyrrolidone (PVP), or combinations thereof. Other mucoadhesive water-erodible polymers may also be used in the present invention. The term "polyacrylic acid" includes both uncrosslinked and partially crosslinked forms, e.g., polycarbophil.

In some embodiments, the mucoadhesive polymeric diffusion environment is a mucoadhesive layer, e.g, a bioerodable mucoadhesive layer. In some embodiments, the devices of the present invention include a bioerodable mucoadhesive layer which comprises a mucoadhesive polymeric diffusion environment.

In some embodiments, the properties of the polymeric diffusion environment are effected by the barrier environment. The barrier environment is disposed such that the flux of medicament is substantially unidirectional. For example, in an exemplary layered device of the present invention, having a layer comprising a medicament dispersed in a polymeric diffusion environment and a co-terminus barrier layer (see, e.g., FIG. 4B), upon application to the mucosa, some medicament may move to and even cross the boundary not limited by the mucosa or barrier layer. In another exemplary layered device of the present invention, a barrier layer does not completely circumscribe the portion of the mucoadhesive polymeric diffusion environment that will not be in direct contact with the mucosa upon application of the device (see, e.g., FIG. 4C). A majority of the medicament in both of these cases, however, flows towards the mucosa. In another exemplary layered device of the present invention, having a barrier layer which circumscribes the portion of the mucoadhesive polymeric diffusion environment that will not be in direct contact with the mucosa upon application of the device (see, e.g., FIG. 4A), upon application to the mucosa, substantially all of the medicament typically flows towards the mucosa.

The barrier environment can be, e.g., a backing layer. A backing layer can be included as an additional layer disposed adjacent to the mucoadhesive polymeric diffusion environment. The layers can be coterminous, or, e.g., the barrier layer may circumscribe the portion of the mucoadhesive polymeric diffusion environment that will not be in direct contact with the mucosa upon application of the device. In one embodiment, the device comprises a backing layer disposed adjacent to the mucoadhesive polymeric diffusion environment. The device of the present invention can also comprise a third layer or coating. A backing layer can be also included in the devices of the present invention as a layer disposed adjacent to a layer which is, in turn, disposed adjacent to the mucoadhesive polymeric diffusion environment (i.e., a three layer device).

In one embodiment, the device further comprises at least one additional layer that facilitates unidirectional delivery of the medicament to the mucosa. In one embodiment, the device of the present invention further comprises at least one additional layer disposed adjacent to the mucoadhesive polymeric diffusion environment. Such layer can include additional medicament or different medicaments, and/or can be present to further reduce the amount of medicament (originally in the mucoadhesive polymeric diffusion environment) that is washed away in the saliva.

Specialty polymers and non-polymeric materials may also optionally be employed to impart lubrication, additional dissolution protection, drug delivery rate control, and other desired characteristics to the device. These third layer or coating materials can also include a component that acts to adjust the kinetics of the erodability of the device.

The backing layer is a non-adhesive water-erodible layer that may include at least one water-erodible, film-forming polymer. In some embodiments, the backing layer will at least partially or substantially erode or dissolve before the substantial erosion of the mucoadhesive polymeric diffusion environment.

The barrier environment and/or backing layer can be employed in various embodiments to promote unidirectional delivery of the medicament (e.g., fentanyl) to the mucosa and/or to protect the mucoadhesive polymeric diffusion environment against significant erosion prior to delivery of the active to the mucosa. In some embodiments, dissolution or erosion of the water-erodible non-adhesive backing layer primarily controls the residence time of the device of the present invention after application to the mucosa. In some embodiments, dissolution or erosion of the barrier environment and/or backing layer primarily controls the directionality of medicament flow from the device of the present invention after application to the mucosa.

The barrier environment and/or backing layer (e.g., a water-erodible non-adhesive backing layer) can further include at least one water erodible, film-forming polymer. The polymer or polymers can include polyethers and polyalcohols as well as hydrogen bonding cellulosic polymers having either hydroxyalkyl group substitution or hydroxyalkyl group and alkyl group substitution preferably with a moderate to high ratio of hydroxyalkyl to alkyl group. Examples include, but are not limited to, hydroxyethyl cellulose (HEC), hydroxypropyl cellulose (HPC), hydroxypropylmethyl cellulose (HPMC), hydroxyethylmethyl cellulose (HEMC), polyvinyl alcohol (PVA), polyethylene glycol (PEG), polyethylene oxide (PEO), ethylene oxide-propylene oxide co polymers, and combinations thereof. The water-erodible non-adhesive backing layer component can optionally be crosslinked. In one embodiment, the water erodible non-adhesive backing layer includes hydroxyethyl cellulose and hydroxypropyl cellulose. The water-erodible non-adhesive backing layer can function as a slippery surface, to avoid sticking to mucous membrane surfaces.

In some embodiments, the barrier environment and/or backing layer, e.g., a bioerodible non-adhesive backing layer, is generally comprised of water-erodible, film-forming pharmaceutically acceptable polymers which include, but are not limited to, hydroxyethyl cellulose, hydroxypropyl cellulose, hydroxypropylmethyl cellulose, hydroxyethylmethyl cellulose, polyvinylalcohol, polyethylene glycol, polyethylene oxide, ethylene oxide-propylene oxide co-polymers, or combinations thereof. The backing layer may comprise other water-erodible, film-forming polymers.

The devices of the present invention can include ingredients that are employed to, at least in part, provide a desired residence time. In some embodiments, this is a result of the selection of the appropriate backing layer formulation, providing a slower rate of erosion of the backing layer. Thus, the non-adhesive backing layer is further modified to render controlled erodibility which can be accomplished by coating the backing layer film with a more hydrophobic polymer selected from a group of FDA approved Eudragit™ polymers, ethyl cellulose, cellulose acetate phthalate, and hydroxyl propyl methyl cellulose phthalate, that are approved for use in other pharmaceutical dosage forms. Other hydrophobic polymers may be used, alone or in combination with other hydrophobic or hydrophilic polymers, provided that the layer derived from these polymers or combination of polymers erodes in a moist environment. Dissolution characteristics may be adjusted to modify the residence time and the release profile of a drug when included in the backing layer.

In some embodiments, any of the layers in the devices of the present invention may also contain a plasticizing agent, such as propylene glycol, polyethylene glycol, or glycerin in a small amount, 0 to 15% by weight, in order to improve the "flexibility" of this layer in the mouth and to adjust the erosion rate of the device. In addition, humectants such as hyaluronic acid, glycolic acid, and other alpha hydroxyl acids can also be added to improve the "softness" and "feel" of the device. Finally, colors and opacifiers may be added to help distinguish the resulting non-adhesive backing layer from the mucoadhesive polymeric diffusion environment. Some opacifers include titanium dioxide, zinc oxide, zirconium silicate, etc.

Combinations of different polymers or similar polymers with definite molecular weight characteristics can be used in order to achieve preferred film forming capabilities, mechanical properties, and kinetics of dissolution. For example, polylactide, polyglycolide, lactide-glycolide copolymers, poly-e-caprolactone, polyorthoesters, polyanhydrides, ethyl cellulose, vinyl acetate, cellulose, acetate, polyisobutylene, or combinations thereof can be used.

The device can also optionally include a pharmaceutically acceptable dissolution-rate-modifying agent, a pharmaceutically acceptable disintegration aid (e.g., polyethylene glycol, dextran, polycarbophil, carboxymethyl cellulose, or poloxamers), a pharmaceutically acceptable plasticizer, a pharmaceutically acceptable coloring agent (e.g., FD&C Blue #1), a pharmaceutically acceptable opacifier (e.g., titanium dioxide), pharmaceutically acceptable anti-oxidant (e.g., tocopherol acetate), a pharmaceutically acceptable system forming enhancer (e.g., polyvinyl alcohol or polyvinyl pyrrolidone), a pharmaceutically acceptable preservative, flavorants (e.g., saccharin and peppermint), neutralizing agents (e.g., sodium hydroxide), buffering agents (e.g., monobasic, or tribasic sodium phosphate), or combinations thereof. Preferably, these components are individually present at no more than about 1% of the final weight of the device, but the amount may vary depending on the other components of the device.

The device can optionally include one or more plasticizers, to soften, increase the toughness, increase the flexibility, improve the molding properties, and/or otherwise modify the properties of the device. Plasticizers for use in the present invention can include, e.g., those plasticizers having a relatively low volatility such as glycerin, propylene glycol, sorbitol, ethylene glycol, diethylene glycol, triethylene glycol, propylene glycol, polypropylene glycol, dipropylene glycol, butylene glycol, diglycerol, polyethylene glycol (e.g., low molecular weight PEG's), oleyl alcohol, cetyl alcohol, cetostearyl alcohol, and other pharmaceutical-grade alcohols and diols having boiling points above about 100° C. at standard atmospheric pressure. Additional plasticizers include, e.g., polysorbate 80, triethyl titrate, acetyl triethyl titrate, and tributyl titrate. Additional suitable plasticizers include, e.g., diethyl phthalate, butyl phthalyl butyl glycolate, glycerin triacetin, and tributyrin. Additional suitable plasticizers include, e.g., pharmaceutical agent grade hydrocarbons such as mineral oil (e.g., light mineral oil) and petrolatum. Further suitable plasticizers include, e.g., triglycerides such as medium-chain triglyceride, soybean oil, safflower oil, peanut oil, and other pharmaceutical agent grade triglycerides, PEGylated triglycerides such as Labrifil®, Labrasol® and PEG-4 beeswax, lanolin, polyethylene oxide (PEO) and other polyethylene glycols, hydrophobic esters such as ethyl oleate, isopropyl myristate, isopropyl palmitate, cetyl ester wax, glyceryl monolaurate, and glyceryl monostearate.

One or more disintegration aids can optionally be employed to increase the disintegration rate and shorten the residence time of the device of the present invention. Disintegration aids useful in the present invention include, e.g., hydrophilic compounds such as water, methanol, ethanol, or low alkyl alcohols such as isopropyl alcohol, acetone, methyl ethyl acetone, alone or in combination. Specific disintegration aids include those having less volatility such as glycerin, propylene glycol, and polyethylene glycol.

One or more dissolution-rate-modifying agents can optionally be employed to decrease the disintegration rate and lengthen the residence time of the device of the present invention. Dissolution-rate modifying agents useful in the present invention include, e.g., hydrophobic compounds such as heptane, and dichloroethane, polyalkyl esters of di and tricarboxylic acids such as succinic and citric acid esterified with C6 to C20 alcohols, aromatic esters such as benzyl benzoate, triacetin, propylene carbonate and other hydrophobic compounds that have similar properties. These compounds can be used alone or in combination in the device of the invention.

The devices of the present invention can include various forms. For example, the device can be a disc or film. In one embodiment, the device comprises a mucoadhesive disc. In one embodiment of the methods and devices of the present invention, the device is a layered, flexible device. The thickness of the device of the present invention, in its form as a solid film or disc, may vary, depending on the thickness of each of the layers. Typically, the bilayer thickness ranges from about 0.01 mm to about 1 mm, and more specifically, from about 0.05 mm to about 0.5 mm. The thickness of each layer can vary from about 10% to about 90% of the overall thickness of the device, and specifically can vary from about 30% to about 60% of the overall thickness of the device. Thus, the preferred thickness of each layer can vary from about 0.005 mm to about 1.0 mm, and more specifically from about 0.01 mm to about 0.5 mm.

In one embodiment, the mucoadhesive polymeric diffusion environment of the device of the present invention has a thickness of about 0.03 mm to about 0.07 mm. In one embodiment, the mucoadhesive polymeric diffusion environment of the device of the present invention has a thickness of about 0.04 mm to about 0.06 mm. In yet another embodiment, the mucoadhesive polymeric diffusion environment of the present invention has a thickness of about 0.05 mm. The thickness of the mucoadhesive polymeric diffusion environment is designed to be thick enough so that it can be easily manufactured, yet thin enough to allow for maximum permeability of the medicament through the layer, and maximum absorption of the medicament into the mucosal layer.

In one embodiment, the backing layer of the device of the present invention has a thickness of about 0.050 mm to about 0.350 mm. In one embodiment, the backing layer of the device of the present invention has a thickness of about 0.100 mm to about 0.300 mm. In yet another embodiment, the backing layer of the present invention has a thickness of about 0.200 mm. The thickness of the backing layer is designed to be thick enough so that it allows for substantially unidirectional delivery of the medicament (towards the mucosa), yet thin enough to dissolve so that it does not have to be manually removed by the subject.

In these embodiments, there is relatively minimal mouth feel and little discomfort because of the thinness and flexibility of the devices as compared to conventional tablet or lozenge devices. This is especially advantageous for patients who have inflammation of the mucosa and/or who may otherwise not be able to comfortably use conventional devices. The devices of the present invention are small and flexible enough so that they can adhere to a non-inflamed area of the mucosa and still be effective, i.e., the mucosa does not need to be swabbed with the device of the present invention.

In various embodiments, the devices of the present invention can be in any form or shape such as a sheet or disc, circular or square in profile or cross-section, etc., provided the form allows for the delivery of the active to the subject. In some embodiments, the devices of the present invention can be scored, perforated or otherwise marked to delineate certain dosages. For example, a device may be a square sheet, perforated into quarters, where each quarter comprises a 200 µg dose. Accordingly, a subject can use the entire device for an 800 µg dose, or detach any portion thereof for a 200 µg, 400 µg or 600 µg dose.

The devices of the present invention can be adapted for any mucosal administration. In some embodiments of the methods and devices of the present invention, the device is adapted for buccal administration and/or sublingual administration.

Yet another advantage of the devices of the present invention is the ease with which they are administered. With conventional devices, the user must hold the device in place, or rub the device over the mucosa for the duration of administration, which may last from twenty to thirty minutes or more. The devices of the present invention adhere to the mucosal surface in less than about five seconds, and naturally erode in about twenty to thirty minutes, without any need to hold the device in place.

Without wishing to be bound by any particular theory, it is also believed that the devices of the present invention are substantially easier to use than devices of the prior art. When devices of the prior art are used, they are often subject to much variability, e.g., due to variation in mouth size, diligence of the subject in correctly administering the device and amount of saliva produced in the subject's mouth. Accordingly, in some embodiments, the present invention provides a variable-free method for treating pain in a subject. The term "variable-free" as used herein, refers to the fact that the devices of the present invention provide substantially similar pharmacokinetic profile in all subjects, regardless of mouth size and saliva production.

Without wishing to be bound by any particular theory, it is also believed that the presence of a backing layer also imparts a resistance to the devices of the present invention. Accordingly, in some embodiments, the devices of the present invention are resistant to the consumption of food or beverage. That is, the consumption of food or beverage while using the devices of the present invention does not substantially interfere with the effectiveness of the device. In some embodiments, the performance of the devices of the present invention, e.g., peak fentanyl concentrations and/or overall exposure to the medicament is unaffected by the consumption of foods and/or hot beverages.

In various embodiments, the devices can have any combination of the layers, ingredients or compositions described herein including but not limited to those described above.

EXEMPLIFICATION

Example 1

Preparation of Devices in Accordance with the Present Invention

Transmucosal devices were configured in the form of a disc, rectangular in shape with round corners, pink on one side and white on the other side. The drug is present in the pink layer, which is the mucoadhesive polymeric diffusion environment, and this side is to be placed in contact with the buccal mucosa (inside the cheek). The drug is delivered into the mucosa as the disc erodes in the mouth. The white side is the non-adhesive, backing layer which provides a controlled erosion of the disc, and minimizes the oral uptake of the drug induced by constant swallowing, thus minimizing or preventing first pass metabolism. The mucoadhesive polymeric diffusion environment and backing layer are bonded together and do not delaminate during or after application.

The backing layer was prepared by adding water (about 77% total formulation, by weight) to a mixing vessel followed by sequential addition of sodium benzoate (about 0.1% total formulation, by weight), methylparaben (about 0.1% total formulation, by weight) and propylparaben (about 0.03% total formulation, by weight), citric acid (about 0.1% total formulation, by weight) and vitamin E acetate (about 0.01% total formulation, by weight), and sodium saccharin (about 0.1% total formulation, by weight). Subsequently, a mixture of the polymers hydroxypropyl cellulose (Klucel EF, about 14% total formulation, by weight) and hydroxyethyl cellulose (Natrosol 250L, about 7% total formulation, by weight) was added and stirred at a temperature between about 120 and 130° F., until evenly dispersed. Upon cooling to room temperature, titanium dioxide (about 0.6% total formulation, by weight) and peppermint oil (about 0.2% total formulation, by weight) were then added to the vessel and stirred. The prepared mixture was stored in an air-sealed vessel until it was ready for use in the coating operation.

The mucoadhesive polymeric diffusion environment was prepared by adding water (about 89% total formulation, by weight) to a mixing vessel followed by sequential addition of propylene glycol (about 0.5% total formulation, by weight), sodium benzoate (about 0.06% total formulation, by weight), methylparaben (about 0.1% total formulation, by weight) and propylparaben (about 0.03% total formulation, by weight), vitamin E acetate (about 0.01% total formulation, by weight) and citric acid (about 0.06% total formulation, by weight), red iron oxide (about 0.01% total formulation, by weight), and monobasic sodium phosphate (about 0.04% total formulation, by weight). After the components were dissolved, 800 µg fentanyl citrate (about 0.9% total formulation, by weight) was added, and the vessel was heated to 120 to 130° F. After dissolution, the polymer mixture [hydroxypropyl cellulose (Klucel EF, about 0.6% total formulation, by weight), hydroxyethyl cellulose (Natrosol 250L, about 1.9% total formulation, by weight), polycarbophil (Noveon AA1 (about 0.6% total formulation, by weight), and carboxy methyl cellulose (Aqualon 7LF, about 5.124% total formulation, by weight)] was added to the vessel, and stirred until dispersed. Subsequently, heat was removed from the mixing vessel. As the last addition step, tribasic sodium phosphate and sodium hydroxide were added to adjust the blend to a desired pH. For example, about 0.6% total formulation, by weight of sodium hydroxide and about 0.4% total formulation, by weight of tribasic sodium phosphate can be added to the formulation. Batches were made having pHs of about 6, 7.25, and 8.5. The blend was mixed under vacuum for a few hours. Each prepared mixture was stored in an air-sealed vessel until its use in the coating operation.

The layers were cast in series onto a St. Gobain polyester liner. First, the backing layer was cast using a knife-on-a-blade coating method. The backing layer was then cured in a continuous oven at about 65 to 95° C. and dried. After two coating and drying iterations, an approximately 8 mil (203 to 213 micrometers) thick backing layer is obtained. Subsequently, the mucoadhesive polymeric diffusion environment was cast onto the backing layer, cured in an oven at about 65 to 95° C. and dried. The devices were then die-cut by kiss-cut method and removed from the casting surface.

Example 2

Study of Fentanyl Citrate Uptake in Humans for Delivery Devices of the Present Invention and a Commercially Available Delivery Device The effect of system pH on the uptake of fentanyl citrate in three exemplary delivery devices of the present invention was evaluated, and compared to that observed in Actiq® Oral Transmucosal Fentanyl Citrate product (Cephalon, Inc., Salt Lake City, Utah), referred to herein as "OTFC". A randomized, open-label, single-dose, four-period, Latin-square crossover study was conducted in 12 healthy volunteers. An Ethical Review Board approved the study and all subjects gave informed consent before participating. Bioanalytical work using a validated liquid chromatography/mass spectrometry/mass spectrometry (LC/MS/MS) method was performed by CEDRA Clinical Research, LLC (Austin, Tex.).

Twelve (9 male, 3 female) healthy volunteers ranging in age from 21 to 44 years were recruited for the instant study.

Subjects tested were free from any significant clinical abnormalities on the basis of medical history and physical examination, electrocardiogram, and screening laboratories. Subjects weighed between about 50 kg and 100 kg and were within 15% of their ideal body weight based on Metropolitan Life tables for height and weight. Subjects were instructed to not consume alcohol, caffeine, xanthine, or foods/beverages containing grapefruit for 48 hours prior to the first dose of study medication and for the entire duration of the study. Subjects were also instructed not to use tobacco or nicotine containing products for at least 30 days prior to the first dose of medication. No subject had participated in any investigational drug study for at least 30 days prior to the instant study; had any significant medical condition either at the time of the study or in the past (including glaucoma and seizure disorders); had a positive drug screen; had used any concomitant medication other than oral contraceptives or acetaminophen for at least 72 hours prior to the first dose; or had a history of allergic reaction or intolerance to narcotics. Premenopausal women not using contraception or having a positive urine beta HCG test were excluded. Table 2, below, shows the demographics of the subjects included in this study.

TABLE 2

Subject Demographics (N = 12)

| | |
|---|---|
| Age, years | |
| Mean (standard deviation) | 32 (7) |
| Median | 31 |
| Range | 21-44 |
| Gender, n (%) | |
| Female | 3 (25) |
| Male | 9 (75) |
| Race, n (%) | |
| Black | 3 (25) |
| Caucasian | 4 (33) |
| Hispanic | 5 (42) |
| Height (cm) | |
| Mean (standard deviation) | 171.6 (9.3) |
| Median | 172.0 |
| Range | 155.0-183.5 |
| Weight (kg) | |
| Mean (standard deviation) | 70.5 (9.0) |
| Median | 70.7 |
| Range | 52.0-86.5 |

The study consisted of a screening visit and a 9-day inpatient period during which each subject received single buccal transmucosal doses of each of the four study treatments with 48 hours separating the doses. The four study treatments, each including 800 μg of fentanyl citrate, were: the OTFC and devices prepared as described in Example 1 and buffered at a pH of about 6 ("device at pH 6"), a pH of about 7.25 ("device at pH 7.25"), and a pH of about 8.5 ("device at pH 8.5").

Subject eligibility was determined at the screening visit, up to 21 days prior to entering the study facility. Subjects arrived at the study facility at 6:00 PM the day prior to dosing (day 0). Predose procedures (physical examination, clinical laboratory tests, electrocardiogram, and substance abuse screen) were performed. After an overnight fast of at least 8 hours, subjects received an oral dose of naltrexone at 6 AM. A standard light breakfast was served approximately 1 hour prior to study drug dosing. A venous catheter was placed in a large forearm or hand vein for blood sampling, and a pulse oximeter and noninvasive blood pressure cuff were attached. Subjects were placed in a semi-recumbent position, which they maintained for 8 hours after each dose.

Subjects received the first dose of drug at 8 AM on day 1 and subsequent doses at the same time on days 3, 5, and 7. Blood samples (7 mL) were collected in ethylenediaminetetraacetic acid (EDTA) for measurement of plasma fentanyl just prior to dose 1 and 5, 7.5, 10, 15, 20, 25, 30, 45, and 60 minutes, and 2, 3, 4, 8, 12, 16, 20, 24, and 48 hours after each dose. The 48-hour post dose sample was collected just prior to administration of the subsequent dose. A total of 511 mL of blood was collected over the study period for pharmacokinetic analysis. Samples were centrifuged and the plasma portion drawn off and frozen at −20° C. or colder.

Finger pulse oximetry was monitored continuously for 8 hours after each dose and then hourly for an additional four hours. If the subject's oxyhemoglobin saturation persistently decreased to less than 90%, the subject was prompted to inhale deeply several times and was observed for signs of decreased oxyhemoglobin saturation. If the oxyhemoglobin saturation value immediately increased to 90% or above, no further action was taken. If the oxyhemoglobin saturation remained below 90% for more than 1 minute, oxygen was administered to the subject via a nasal cannula. Heart rate, respiratory rate, and blood pressure were measured just prior to the dose, and every 15 minutes for 120 minutes, and at 4, 6, 8, and 12 hours post dose. Throughout the study, subjects were instructed to inform the study personnel of any adverse events.

Each subject received a single buccal dose of each of the 4 study treatments in an open-label, randomized crossover design. The measured pH on the three devices during the manufacturing process in accordance with Example 1 were 5.95 for the device at pH 6.0, 7.44 for the device at pH 7.25, and 8.46 for the device at pH 8.5. After subjects rinsed their mouths with water, the delivery devices of the present invention were applied to the oral mucosa at a location approximately even with the lower teeth. The devices were held in place for 5 seconds until the device was moistened by saliva and adhered to the mucosa membrane. After application, subjects were instructed to avoid rubbing the device with their tongues, as this would accelerate the dissolution of the device.

OTFC doses were administered according to the package insert. After each mouth was rinsed with water, the OTFC unit was placed in the mouth between the cheek and lower gum. The OTFC unit was occasionally moved from one side of the mouth to the other. Subjects were instructed to suck, not chew, the OTFC unit over a 15-minute period. To block the respiratory depressive effects of fentanyl, a 50 mg oral dose of naltrexone was administered to each subject at approximately 12 hours and 0.5 hours prior to each dose of study drug and 12 hours after study drug. Naltrexone has been shown not to interfere with fentanyl pharmacokinetics in opioid naïve subjects. Lor M, et al., *Clin Pharmacol Ther;* 77: P76 (2005).

At the end of the study, EDTA plasma samples were analyzed for plasma fentanyl concentrations using a validated liquid chromatography with tandem mass spectrophotometry (LC/MS/MS) procedure. Samples were analyzed on a SCIEX API 3000 spectrophotometer using pentadeuterated fentanyl as an internal standard. The method was validated for a range of 0.0250 to 5.00 ng/mL based on the analysis of 0.500 mL of EDTA human plasma. Quantitation was performed using a weighted $(1/X^2)$ linear least squares regression analysis generated from calibration standards.

Pharmacokinetic data were analyzed by noncompartmental methods in WinNonlin (Pharsight Corporation). In the pharmacokinetic analysis, concentrations below the limit of quantitation (<0.0250 ng/mL) were treated as zero from time-zero up to the time at which the first quantifiable concentration ($C_{first}$) was observed. Subsequent to $C_{first}$, concentrations below this limit were treated as missing. Full precision concentration data were used for all pharmacokinetic and statistical analyses. $C_{first}$ was defined as the first quantifiable concentration above the pre-dose concentration because quantifiable data were observed in the pre-dose samples in some subjects. $\lambda_z$ was calculated using unweighted linear regression analysis on at least three log-transformed concentrations visually assessed to be on the linear portion of the terminal slope. The $t_{1/2}$ was calculated as the ratio of 0.693 to $\lambda_z$. Pharmacokinetic parameters were summarized by treatment using descriptive statistics. Values of $t_{first}$, $t_{max}$, $C_{max}$, and $AUC_{inf}$ of the three exemplary devices of the present invention were compared to OTFC using an analysis of variance (ANOVA) model and Tukey's multiple comparison test. Statistical analysis was performed using SAS (SAS Institute Inc.). Table 3, below, presents the fentanyl pharmacokinetics for all 4 treatments after a single dose.

dose; calculated using the linear trapezoidal rule and extrapolated using the elimination rate constant if quantifiable data were not observed through 24 hours; $AUC_{last}$ is the area under the concentration-time curve from time zero to the time of the last quantifiable concentration; calculated using the linear trapezoidal rule; $AUC_{inf}$ is the area under the concentration-time curve from time zero extrapolated to infinity, calculated as $AUC_{last}+C_{last}/\lambda_z$; $AUC_{extrap}$ (%) is the percentage of $AUC_{inf}$ based on extrapolation; MRT is the mean residence time, calculated as $AUMC_{inf}/AUC_{inf}$, where $AUMC_{inf}$ is the area under the first moment curve (concentration-time vs. time), calculated using the linear trapezoidal rule form time zero to $T_{last}$ ($AUMC_{last}$) and extrapolated to infinity. It should be noted that, because quantifiable data were observed in the pre-dose samples for some subjects, $C_{first}$ was redefined as the first quantifiable concentration above the pre-dose concentration, which was set to zero in calculating mean fentanyl concentrations.

FIG. 1 illustrates the plasma fentanyl concentration from 0 to 48 hours post-dose for the OTFC dose and the doses provided by the three exemplary devices of the present invention. The device at pH 7.25 provided the highest peak concentrations of fentanyl of the three devices of the present invention used in this study. In general, OTFC provided

TABLE 3

Pharmacokinetic Parameters of OTFC and Three Formulations of BEMA Fentanyl Citrate

| Parameter | OTFC 800 µg (N = 12) | | Device at pH 6 Fentanyl 800 µg (N = 12) | | Device at pH 7.25 Fentanyl 800 µg (N = 12) | | Device at pH 8.5 Fentanyl 800 µg (N = 12) | |
|---|---|---|---|---|---|---|---|---|
| | Mean (SD) | CV % | Mean (SD) | CV % | Mean (SD) | CV % | Mean (SD) | CV % |
| $t_{first}$ (hr) | 0.23 (0.18) | 78.03 | 0.13 (0.04) | 27.99 | 0.15 (0.08) | 54.18 | 0.21 (0.11) | 55.21 |
| $C_{first}$ (ng/mL) | 0.07 (0.05) | 64.95 | 0.05 (0.02) | 35.25 | 0.06 (0.02) | 41.59 | 0.06 (0.02) | 30.08 |
| $t_{max}$ (hr) | 2.28 (1.32) | 58.04 | 2.15 (1.14) | 53.23 | 1.61 (1.04) | 64.49 | 2.21 (1.34) | 60.64 |
| $C_{max}$ (ng/mL)[1] | 1.03 (0.25) | 24.19 | 1.40 (0.49) | 35.12 | 1.67 (0.75) | 45.07 | 1.39 (0.41) | 29.44 |
| $AUC_{last}$ (hr · ng/mL) | 9.04 (3.53) | 39.01 | 12.17 (4.28) | 35.19 | 12.98 (5.59) | 43.04 | 11.82 (4.54) | 38.37 |
| $AUC_{0-24}$ (hr · ng/mL) | 7.75 (2.52) | 32.48 | 10.43 (3.00) | 28.74 | 11.38 (4.30) | 37.78 | 10.18 (3.20) | 31.44 |
| $AUC_{inf}$ (hr · ng/mL) | 10.30 (3.84) | 37.29 | 13.68 (4.55) | 33.24 | 14.44 (5.39) | 37.33 | 13.11 (4.77) | 36.40 |
| % $AUC_{extrap}$ | 12.15 (8.31) | 68.40 | 11.53 (6.84) | 59.33 | 11.72 (6.91) | 58.96 | 10.31 (4.49) | 43.49 |
| $\lambda z$ (hr$^{-1}$) | 0.05 (0.02) | 37.83 | 0.05 (0.02) | 31.10 | 0.05 (0.01) | 21.18 | 0.06 (0.02) | 26.98 |
| $t_{1/2}$ (hr) | 15.33 (6.85) | 44.67 | 15.12 (5.09) | 33.66 | 14.28 (2.75) | 19.23 | 13.33 (4.14) | 31.04 |
| MRT | 15.92 (6.17) | 38.73 | 15.73 (4.19) | 26.63 | 14.45 (3.12) | 21.61 | 14.31 (4.45) | 31.09 |

[1]Mean differences of BEMA fentanyl formulations and OTFC significantly different by ANOVA, p = 0.0304.

Abbreviations used herein are as follows: $C_{first}$ is the first quantifiable drug concentration in plasma determined directly from individual concentration-time data; $t_{first}$ is the time to the first quantifiable concentration; $C_{max}$ is the maximum drug concentration in plasma determined directly from individual concentration-time data; $t_{max}$ is the time to reach maximum concentration; $\lambda_z$ is the observed elimination rate constant; $t_{1/2}$ is the observed terminal elimination half-life calculated as $\ln(2)/\lambda_z$; $AUC_{0-24}$ is the area under the concentration-time curve from time zero to 24 hours post-lower fentanyl concentrations for most time points as compared with the devices of the present invention. The device at pH 6 and the device at pH 8.5 yielded very similar concentration-time profiles, with $C_{max}$ values of 1.40 ng/mL and 1.39 ng/mL, respectively. These values are midway between the maximum plasma fentanyl values of 1.03 ng/mL for OTFC and 1.67 ng/mL for the device at pH 7.25. After approximately 6 hours post-dose, the fentanyl concentration-time profiles for the three devices of the present invention were similar. The differences in fentanyl $C_{max}$ values were statistically significant when comparing all of the devices of the present invention to OTFC (p=0.0304), and for pairwise comparisons of the device at pH 7.25 to OTFC (p<0.05).

In general, quantifiable fentanyl concentrations were observed earlier after administration of one of the three exemplary devices of the present invention (mean $t_{first}$ of 8 to 13 minutes) compared with OTFC (mean $t_{first}$ of 14 minutes). The device at pH 7.25 yielded the earliest average $t_{max}$ (1.61 hours) and highest $C_{max}$ (mean 1.67 ng/mL). As shown in FIG. 2, fentanyl absorption from a device at pH 7.25 was more rapid over the first hour post dose than from OTFC, with 30-minute mean plasma concentrations of 0.9 ng/mL for the device at pH 7.25 and 0.5 ng/mL for OTFC.

The delivery devices of the present invention provided overall greater exposure to fentanyl, based on $AUC_{0-24}$ as compared to OTFC. Fentanyl exposure as measured by $AUC_{0-24}$ values, were similar across groups treated with one of the devices of the present invention, suggesting that comparable amounts of fentanyl enter the systemic circulation from each of the devices. The device at pH 7.25, however, demonstrated approximately 19% greater maximum plasma fentanyl concentration.

Overall, fentanyl concentrations were observed earlier and increased more rapidly after administration of a device of the present invention compared with OTFC. Mean 30 and 60 minute plasma fentanyl concentrations observed with use of the device at pH 7.25 were 1.8 and 1.7 times higher than with OTFC, respectively. Similarly, the maximum plasma fentanyl concentration was 60% higher using a device of the present invention (mean 1.67 ng/mL) when compared to use of OTFC (mean 1.03 ng/mL). The $C_{max}$ for OTFC identified in this study is nearly identical to the 1.1 ng/mL $C_{max}$ value reported by Lee and co-workers with both a single 800 mcg lozenge as well as two 400 mcg lozenges. Lee, M., et al., *J Pain Symptom Manage* 2003; 26:743-747. Overall, fentanyl exposure for the fentanyl formulations of the present invention were greater than for OTFC. Mean estimates of $AUC_{last}$ and $AUC_{inf}$ were slightly larger, but the same general trends were observed. This indicates that the transmucosal uptake is significantly improved in the devices of the present invention as compared to OTFC.

Mean $t_{1/2}$ values and MRT values were similar for all treatment groups and the values in both cases followed the same trend. Additionally, because MRT after extravascular administration is dependent on the absorption and elimination rates, the MRT values suggest that fentanyl absorbs faster from a delivery device of the present invention, particularly with the device at pH 7.25 and the device at pH 8.5. This observation is consistent with the $t_{max}$ for the delivery devices of the present invention relative to OTFC.

Adverse events were similar across treatment groups and confounded by the co-administration of naltrexone with each study treatment. The most frequent adverse events were sedation and dizziness. One subject experienced oral mucosal irritation with OTFC. No subject experienced mucosal irritation with any of the three exemplary devices of the present invention. All reported adverse events were mild or moderate in nature.

As demonstrated above, the delivery devices of the present invention provide significantly higher plasma fentanyl concentrations than OTFC. The delivery device at pH 7.25 appeared to provide enhanced uptake believed to be attributable to a favorable balance between drug solubility and ionization. Similar studies have shown that the delivery devices of the present invention provide an absolute bioavailability of about 70.5% and buccal absorption was about 51% (estimated by subtracting the $AUC_{inf}$ following an oral dose of fentanyl from the $AUC_{inf}$ following BEMA fentanyl applied to the buccal mucosa, dividing by the single disc BEMA Fentanyl $AUC_{inf}$, and multiplying by 100).

Example 3

Preparation of Devices in Accordance with the Present Invention

Devices containing buprenorphine were also produced using the same method as described in Example 1, except that buprenorphine was added to the mucoadhesive polymeric diffusion environment, rather than fentanyl citrate.

Example 4

Study of Buprenorphine Uptake in Humans for Delivery Devices of the Present Invention A study similar to that described in Example 2 was also performed with buprenorphine in exemplary devices of the present invention (at pH 6 and 7.25), suboxone sublingual and buprenex intramuscular. Results from this study are summarized in the graph in FIG. 3. As demonstrated in Table 4, the delivery devices of the present invention at pH 6 appeared to provide enhanced uptake believed to be attributable to a favorable balance between drug solubility and ionization.

TABLE 4

| Pharmacokinetic data for buprenorphine | | |
|---|---|---|
| pH | 6 | 7.25 |
| $t_{first}$ (hr) | 0.75 | 0.75 |
| $C_{first}$ (ng/mL) | 0.0521 | 0.0845 |
| $t_{max}$ (hr) | 3 | 3 |
| $C_{max}$ (ng/mL)[1] | 1.05 | 0.86 |

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. A method for delivering fentanyl to a human comprising:
    administering a mucoadhesive biodegradable drug delivery device for transmucosal delivery to the oral mucosa of said human, the device comprising:
        a biodegradable mucoadhesive layer comprising fentanyl disposed in a polymeric diffusion environment, wherein the polymeric diffusion environment has a pH of between about 6 and about 8.5; and
        a polymeric barrier environment disposed adjacent to the mucoadhesive layer, wherein a unidirectional diffusion gradient of fentanyl is provided upon application to a buccal surface,
    wherein the overall bioavailability of fentanyl is at least about 60%; and
    wherein the fentanyl is delivered in less than about 30 minutes.

2. The method of claim 1, wherein the overall bioavailability of fentanyl is at least about 70%.

3. The method of claim 1, wherein the polymeric diffusion environment comprises at least one film-forming water-erodible adhesive polymer and at least one bioadhesive polymer.

4. The method of claim 1, wherein said polymeric barrier environment comprises at least one film-forming water-erodible polymer.

5. The method of claim 1, wherein the polymeric diffusion environment has a pH of between about 7 to about 7.5.

6. The method of claim 1, wherein the mucoadhesive biodegradable drug delivery device further comprises an opioid antagonist.

7. The method of claim 1, wherein the biodegradable drug delivery device further comprises a third layer or coating.

8. The method of claim 1, wherein the polymeric diffusion environment has a pH buffered to between about 6 and about 8.5.

9. The method of claim 1, wherein the polymeric diffusion environment has a pH buffered to between about 7 to about 7.5.

10. The method of claim 8, wherein the overall bioavailability of fentanyl is at least about 70%.

11. The method of claim 8, wherein the polymeric diffusion environment comprises at least one film-forming water-erodible adhesive polymer and at least one bioadhesive polymer.

12. The method of claim 8, wherein said polymeric barrier environment comprises at least one film-forming water-erodible polymer.

13. The method of claim 8, wherein the mucoadhesive biodegradable drug delivery device further comprises an opioid antagonist.

14. The method of claim 8, wherein the biodegradable drug delivery device further comprises a third layer or coating.

15. A device for delivering fentanyl to a human, the device comprising:
    a biodegradable mucoadhesive layer comprising fentanyl disposed in a polymeric diffusion environment, wherein the polymeric diffusion environment has a pH of between about 6 and about 8.5; and
    a polymeric barrier environment disposed adjacent to the mucoadhesive layer, wherein a unidirectional diffusion gradient of fentanyl is provided upon application to a buccal surface of a subject,
    wherein upon application to a buccal surface, the overall bioavailability of fentanyl is at least about 60%; and
    wherein the fentanyl is delivered in less than about 30 minutes.

16. The device of claim 15, wherein the overall bioavailability of fentanyl is at least about 70%.

17. The device of claim 15, wherein the polymeric diffusion environment comprises at least one film-forming water-erodible adhesive polymer and at least one bioadhesive polymer.

18. The device of claim 15, wherein said polymeric barrier environment comprises at least one film-forming water-erodible polymer.

19. The device of claim 15, wherein the polymeric diffusion environment has a pH of between about 7 to about 7.5.

20. The device of claim 15, wherein the mucoadhesive biodegradable drug delivery device further comprises an opioid antagonist.

21. The device of claim 15, wherein the biodegradable drug delivery device further comprises a third layer or coating.

22. The device of claim 15, wherein the polymeric diffusion environment has a pH buffered to between about 6 and about 8.5.

23. The device of claim 15, wherein the polymeric diffusion environment has a pH buffered to between about 7 to about 7.5.

24. The device of claim 22, wherein the overall bioavailability of fentanyl is at least about 70%.

25. The device of claim 22, wherein the polymeric diffusion environment comprises at least one film-forming water-erodible adhesive polymer and at least one bioadhesive polymer.

26. The device of claim 22, wherein said polymeric barrier environment comprises at least one film-forming water-erodible polymer.

27. The device of claim 22, wherein the mucoadhesive biodegradable drug delivery device further comprises an opioid antagonist.

28. The device of claim 27, wherein said opioid antagonist is naloxone.

29. The device of claim 22, wherein the biodegradable drug delivery device further comprises a third layer or coating.

30. A method for treating pain, the method comprising:
    adhering a mucoadhesive biodegradable drug delivery device to a buccal surface of a human, the device comprising:
        a biodegradable mucoadhesive layer comprising a therapeutically effective amount of fentanyl for treating pain disposed in a polymeric diffusion environment, wherein the polymeric diffusion environment has a pH buffered to between about 6 and about 8.5; and a polymeric barrier environment disposed adjacent to the mucoadhesive layer wherein a unidirectional diffusion gradient of fentanyl is provided upon application to the buccal surface, wherein the transmucosal delivery of fentanyl is at least about 50% by direct buccal absorption, wherein the overall bioavailability of fentanyl is at least about 70%; and wherein the fentanyl is delivered in less than about 30 minutes.

* * * * *